(12) United States Patent
Rise

(10) Patent No.: US 6,263,237 B1
(45) Date of Patent: Jul. 17, 2001

(54) TECHNIQUES FOR TREATING ANXIETY DISORDERS BY BRAIN STIMULATION AND DRUG INFUSION

(75) Inventor: Mark T. Rise, Monticello, MN (US)

(73) Assignee: Medtronic, Inc., Minneapolis, MN (US)

(*) Notice: Subject to any disclaimer, the term of this patent is extended or adjusted under 35 U.S.C. 154(b) by 0 days.

(21) Appl. No.: 09/503,530

(22) Filed: Feb. 14, 2000

Related U.S. Application Data

(62) Division of application No. 08/847,212, filed on Dec. 23, 1997, now Pat. No. 6,128,537.

(51) Int. Cl.[7] .................................................. A61N 1/18
(52) U.S. Cl. .................................. 607/3; 607/45; 607/72; 128/898; 604/21; 604/49
(58) Field of Search ................................ 617/3–5, 45, 72, 617/115–117, 120, 153; 128/898; 604/20, 21, 49–53, 890.1, 891.1, 892.11, 65–67, 93, 246

(56) References Cited

U.S. PATENT DOCUMENTS

| | | | |
|---|---|---|---|
| 3,850,161 | 11/1974 | Liss ................................ | 128/2.1 R |
| 4,692,147 | 9/1987 | Duggan ........................... | 604/93 |
| 4,867,164 | 9/1989 | Zabara ............................ | 128/421 |
| 4,892,538 | * 1/1990 | Aebischer et al. .............. | 604/891.1 |
| 5,011,472 | * 4/1991 | Aebischer et al. .............. | 604/50 |
| 5,025,807 | 6/1991 | Zabara ............................ | 128/421 |
| 5,458,629 | 10/1995 | Baudino et al. ................. | 607/116 |
| 5,470,846 | 11/1995 | Sandyk ............................ | 514/159 |
| 5,998,630 | * 12/1999 | Fritz et al. ...................... | 548/569 |
| 6,046,215 | * 4/2000 | Audia et al. .................... | 514/337 |

FOREIGN PATENT DOCUMENTS

| | | | |
|---|---|---|---|
| WO 94/01166 | 1/1994 | (WO) ........................ | A61M/31/00 |

OTHER PUBLICATIONS

Mueller, et al., "Skin Impedance in Relation to Pain Threshold Testing by Electrical Means[1] " Journal of Applied Physiology, vol. 5, pp. 746–752, 1953.

Laitinen et al., "Intraoperative Electrical Stimulation of the Brain in Patients with Obsessive–Compulsive Neurosis", Appl. Neurophysiol. 51(6): 317–23, Nov.–Dec. (1988).

Andy, O.J., "Thalamic Stimulation for Control of Movement Disorders" Applied Neurophysiology, 46107–111 (1983).

Alexander, et al., "Functional Architecture of Basal Ganglia Circuits" Neural Substrates of Parallel Processing TINS, vol. 13, No. 7, 1990 pp. 266–276.

Graham, et al., "Injection of Ecitatory Amno Acid Antagonists into the Medial Pallidal Segment of A 1–methyl–4–phenyl–1,2,3,6–tetrahydropyridine (MPTP) Treated Primate Reverses Motor Symptoms of Parkinsonism" Life Sciences, vol. 47, pp. PL–91 –PL–97 (1990).

(List continued on next page.)

*Primary Examiner*—Jeffrey R. Jastrzab
(74) *Attorney, Agent, or Firm*—Eric R. Waldkoetter; Tom G. Berry; Curtis D. Kinghorn

(57) ABSTRACT

Techniques using one or more drugs and/or electrical stimulation for treating an anxiety disorder by means of an implantable signal generator and electrode and/or an implantable pump and catheter. A catheter is surgically implanted in the brain to infuse the drugs, and one or more electrodes may be surgically implanted in the brain to provide electrical stimulation.

20 Claims, 19 Drawing Sheets

OTHER PUBLICATIONS

Crossman, et al., "Experimental Hemiballismus in the Baboon Produced by Injection of a Gamma–Aminobutyric Acid Antagonist in the Basal Ganglia" Neuroscience Letters, 20 pp. 369–372 (1980).

Duncan, et al., "Thalamic VPM Nucleus in the Behaving Monkey. III. Effects of Reversible Inactivation by Lidocaine on Thermal and Mechanical Discrimination" Journal of Neurophysiology vol. 70, No. 5 Nov. 1993 pp. 2086–2096.

Bobo, et al., "Convection–Enhanced Delivery of Macromolecules in the Brain" Proc. Natl., Acad. Sci USA, vol. 91 pp. 2076–2080, Mar. 1994 Applied Biological Sciences.

van Horne, et al., "Multichannel Semiconductor–Based Electrodes for in vivo Electrochemical and Electrophysiological Studies in rat CNS" Neuroscience Letters, 120 (1990) pp. 249–252.

Benabid, et al., "Long–term Suppression of Tremor by Chronic Stimulation of the Ventral Intermediate Thalamic Nucleus" The Lancet, vol. 337, Feb. 16, 1991 pp. 403–406.

Martinez et al., "Toxicology Kinetics of Long–Term Intraventricular Infusion of Phenytoin and Valproic Acid in Pigs: Experimental Study" Acta Neurochirurgica Suppl. 52, pp. 3–4 (1991).

* cited by examiner

TECHNIQUES FOR TREATING ANXIETY DISORDERS BY BRAIN STIMULATION AND DRUG INFUSION

This application is a Divisional of application Ser. No. 08/847,212 filed Dec. 23, 1997 now U.S. Pat. No. 6,128,537.

BACKGROUND OF THE INVENTION

1. Field of the Invention

This invention relates to nerve tissue stimulation and infusion techniques, and more particularly relates to such techniques for treating anxiety disorders, including generalized anxiety disorder, obsessive-compulsive disorders, panic attacks and phobias.

2. Description of the Related Art

Some people suffer from chronic intractable anxiety disorders. The key feature of anxiety disorders is the frequent occurrence of the symptoms of fear; arousal, restlessness, heightened responsiveness, accelerated heart beat, elevated blood pressure, sweating, a desire to run or escape and avoidance behavior. Generally, anxiety is a normal response to certain life situations and can be beneficial to the person experiencing it. However, excessive or inappropriate anxiety can be detrimental. Anxiety disorders are the most common psychiatric disorders, affecting between 10 to 30 percent of the general population (Robins et. al., Arch Gen Psychiatry 1984; 41:949–958). These disorders include generalized anxiety, phobias, panic attacks, and obsessive-compulsions.

Generalized anxiety is characterized by unrealistic or excessive worry, lasting long periods of time (i.e. months). The symptoms of generalized anxiety are excessive muscle tension; overactivity in the autonomic nervous system evidenced by shortness of breath, sweating, cold hands, hyperventilation and tachycardia; and increased vigilance manifest as an increased startle response or difficulty in concentrating. Generalized anxiety is treated with oral medications from the benzodiazepine category such as chlordiazepoxide (Librium®) and diazepam (Valium®). These drugs have been shown to act by enhancing the activity of $GABA_A$ receptors leading to a hyperpolarization of neurons. The specific neurons affected are believed to be located in the amygdala which is part or the limbic system, a subset of the brain thought to be of central importance for emotional behavior.

In contrast to generalized anxiety, panic attacks are brief, recurrent episodes of terror. The symptoms include tachycardia, a feeling of "shortness of breath" that leads to hyperventilation (which can lead to unconsciousness), dizziness, trembling, flushes or chills, chest pain and a fear of dying or of going crazy or of doing something uncontrolled. Persons suffering from panic attacks may also experience generalized anxiety anticipating the occurrence of a panic attack. Finally, for some persons the occurrence of panic attacks may be associated with specific situations in which the panic attacks have occurred in the past. This association may become so strong that the person rigidly avoids the situation associated with the panic attacks. This results in the third component of the panic disorder cascade, a phobia for the situation.

A phobic reaction is a neurotic disorder characterized by an intense, persistent fear of some object or situation in which the fear is out of proportion to any real danger, is inconsistent with the persons general personality, is consciously recognized as unfounded, and frequently interferes with the patient's activities. The person may experience all the symptoms of anxiety described above. Phobias can include fear of places such as agoraphobia (fear of open spaces), acrophobia (fear of heights), achluophobia (fear of darkness) or potamophobia (fear of lakes). Alternatively, the phobia may represent a fear of a loss of control such as the fear of infection (molysmophobia) or lightning (astraphobia). In phobias, the person's anxiety is fixed to some symbolic object or situation, so that the anxiety may be controlled by avoiding the feared object or situation. The origin of the anxiety may be conscious or unconscious.

Obsessive-compulsive disorder (OCD) is a relatively frequent anxiety disorder characterized by the presence of intrusive and senseless ideas, thoughts, urges, and images (obsessions), as well as by repetitive cognitive and physical activities that are performed in a ritualistic way (compulsions) usually in an attempt to neutralize anxiety caused by obsession (American Psychiatric Association. Diagnostic and statistical manual of mental disorders. 4th ed. Washington, D.C.: American Psychiatric Association, 1994.) Examples of obsessive-compulsions are a compulsive washing of the hands or counting or ruminating about disease or sexual behavior perhaps manifest as repeated testing for AIDS. The symptoms are often concealed from others with the rituals confined to private hours but can become disruptive to school or work as the ability to control the rituals fades.

Neuroscientists are beginning to understand the neural circuitry of the brain that controls anxiety. The structures of the brain involved include the limbic system, the frontal lobes of the cortex, parts of the thalamus and basal ganglia, the locus coeruleus, dorsal raphe nucleus and the white mater connections between them such as the internal capsule and cingulum. While the general areas involved are beginning to be recognized, much is unknown about the specific functions of the areas and the nature of the signals between them.

Neurosurgeons have achieved success treating chronic intractable anxiety disorders by creating surgical lesions at specific locations in this circuitry. Procedures that have been tried and found to be at least partially successful include anterior capsulotomy, cingulotomy, subcaudate tractotomy, and a combination of the cingulotomy and subcaudate tractotomy called a limbic leucotomy. For the most part these surgical procedures result in a destruction of the fiber pathways connecting various regions of the nervous system included in the list given above. Laiteinen and Singounas (*Applied Neruophysiol,* 51(6):317–323, November–December 1988) tried brief stimulation intraoperatively with three to six second trains of 60 pulses per second monophasic pulses. This stimulation was applied with the patient awake at the lesion targets of the anterior limb of the internal capsule, middle anterior cingulum, rostral cingulum or the knee of the corpus callosum just prior to carrying out the lesion. Of twenty patients stimulated, three reported reduced anxiety and one reported an increase in anxiety. Electrical stimulation of nerve cells to activate them has been practiced nearly since the discovery of electricity. Benabid (*The Lancet,* Vol. 337, 403–406, Feb. 16, 1991) and Andy (*Appl. Neurophysiol.* 46, 107– 111 1983 have shown more recently that stimulation of nerve cells in certain nuclei such as the ventral lateral thalamus, subthalamic nucleus, and internal segment of the globus pallidus at higher pulse frequencies can have the same effect as a functional lesion. This technique has been used to treat certain movement disorders.

Focal release of pharmaceutical agents through infusion pumps is used to treat pain and spasticity. Rise and Elsberry have proposed using infusion pumps to deliver pharmaceuticals focally to treat movement disorders as disclosed in U.S. Pat. No. 5,832,932 "Method Of Treating Movement Disorders By Brain Infusion" Nov. 10, 1998), and Rise and Ward have proposed focal delivery of medications to treat Epilepsy as disclosed in U.S. Pat. No. 5,713,923 "Techniques For Treating Epilepsy By Brain Stimulation And Drug Infusion" (Feb. 3, 1998). Abeschier (WO 94/01166) has proposed as a method to treat disorders of movement and epilepsy by using encapsulated cells which secrete neuroinhitory agents or polymer matrices loaded with neuroinhibitory agents.

Smulevich et. al. ("Psychotropic drug therapy using maintenance dosage pumps" *Nevropathol Psikhiatr* 1987, 87 (6) p888–93, Issn 0044-4588) have used an implantable pump for subcutaneous delivery of psychotropic drugs. They found this technique particularly useful when providing " . . . functional training of patients with phobic abnormalities."

SUMMARY OF THE INVENTION

A preferred form of the invention uses one or more drugs and/or electrical stimulation to treat an anxiety disorder. The treatment is carried out by an implantable pump and a catheter having a proximal end coupled to the pump and having a discharge portion for infusing therapeutic dosages of the one or more drugs into a predetermined infusion site in brain tissue. Alternatively, encapsulated cells selected to secrete the appropriate substance or a drug eluting polymer may be implanted into a predetermined treatment site in brain tissue. The treatment also may be carried out by an implantable signal generator and an implantable electrode having a proximal end coupled to the signal generator and having a stimulation portion for electrically stimulating a predetermined stimulation site in the brain tissue. In one embodiment of the invention stimulation and/or infusion is carried out in a nearly continuous manner. In another form of the invention, the stimulation or infusion is initiated by the patient in response to anxiety related symptoms or anxiety provoking situations.

Another form of the invention uses a sensor in combination with the signal generator, one or more stimulating electrodes, pump and catheter to treat a neurological disorder. In this form of the invention, the sensor generates a sensor signal related to a condition resulting from the anxiety disorder. Control means responsive to the sensor signal regulate the signal generator and pump so that the neurological disorder is treated and the symptoms of the various anxiety disorders, including generalized anxiety, panic attacks, phobias and obsessive-compulsive disorders, can be alleviated or prevented By using the foregoing techniques, the symptoms of the various anxiety disorders, including generalized anxiety, panic attacks, phobias and obsessive-compulsive disorders, can be controlled to a degree unattainable by prior art methods or apparatus.

BRIEF DESCRIPTION OF THE DRAWINGS

These and other advantages and features of the invention will become apparent upon reading the following detailed description and referring to the accompanying drawings in which like numbers refer to like parts throughout and in which.

DESCRIPTION OF THE PREFERRED EMBODIMENTS

Figure 1:
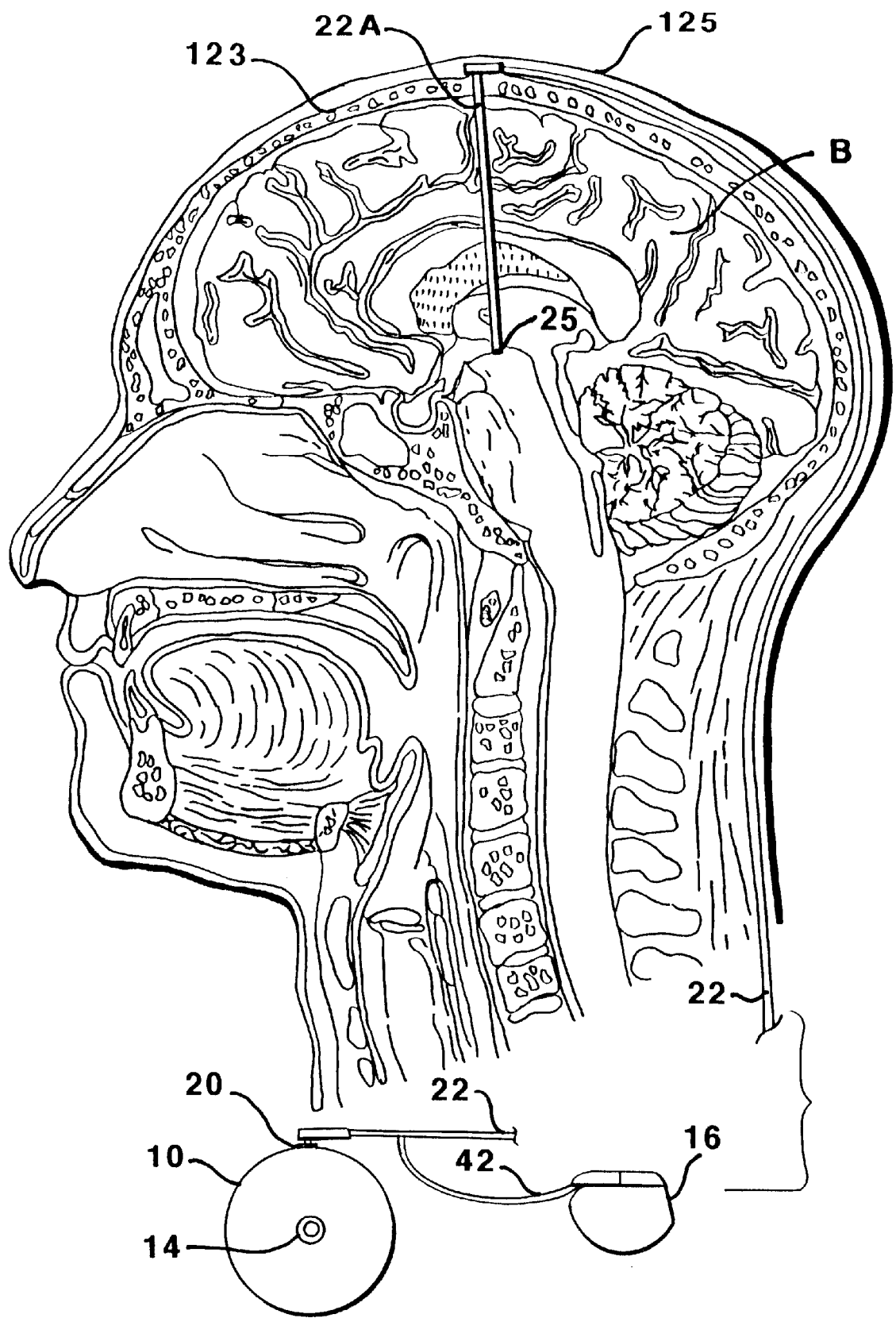
FIG. 1 is a diagrammatic illustration of a combined catheter and electrode implanted in a brain according to a preferred embodiment of the present invention, and a signal generator and pump coupled to the combined catheter and electrode.

Referring to FIG. 1, a pump or device 10 made in accordance with the preferred embodiment may be implanted below the skin of a patient. The device has a port 14 into which a hypodermic needle can be inserted through the skin to inject a quantity of a liquid agent, such as a medication or drug. The liquid agent is delivered from device 10 through a catheter port 20 into a catheter 22. Catheter 22 is positioned to deliver the agent to specific infusion sites in a brain (B). Device 10 may take the form of the like-numbered device shown in U.S. Pat. No. 4,692,147 (Duggan) ("the '147 Patent"), assigned to Medtronic, Inc., Minneapolis, Minn., which is incorporated by reference. An embodiment of pump 10 may be found in the Synchromed™ Infusion System manufactured by Medtronic, Inc. of Minneapolis, Minn. However, pump 10 may take the form of any device used for moving fluid from a reservoir.

The distal end of catheter 22 terminates in a cylindrical hollow tube 22A having a distal end 25 implanted into a portion of the brain by conventional stereotactic surgical techniques. A hemispherical portion 23 (FIG. 3) at the distal end 25 of tube 22A provides a rounded profile for minimizing tissue disruption during insertion. End 25 is provided with microporous portions 27–29 (FIG. 3) to allow infusion and filtering of a liquid agent. Microporous portions 27–29 are preferably composed of a porous material such as polysulfone hollow fiber, manufactured by Amicon, although polyethylene, polyarnides, polypropylene and expanded polytetrafluorethylene (ePTFE) are also suitable.

In a preferred embodiment, the preferred pore size is approximately less than or equal to 0.22 microns. It is preferred that the maximum pore size be less than or equal to approximately 0.22 microns to prevent any derelict bacterial agents that may be present inside the catheter 22A from entering into the brain B. Furthermore, at larger pore sizes, there is the potential for tissue in-growth that may restrict the flow of agents out of the microporous portions 27–29. Alternatively, end 25 may be provided with multiple holes or slits in which case filtering of the liquid agent may occur within pump 10.

Catheter 22 could take the form of a lead catheter combination developed for use outside of the dural covering of the spinal cord to treat pain which is shown in FIG. 1 in U.S. Pat. No. 5,423,877 (Mackey) which is incorporated by reference. Alternatively, catheter 22 could take the form depicted in FIGS. 1–4 in U.S. Pat. Nos. 5,119,832 and 5,458,631 (Xavier) which is incorporated by reference also developed for use outside of the dura to treat pain in which the center lumen 34 terminates in a single opening at the distal end 25 of catheter 22A Referring to FIG. 2, tube 22A includes an outer cylindrical insulating jacket 30 and an inner cylindrical insulating jacket 32 that defines a cylindrical catheter lumen 34. A multifilar coil of wire 36 is embedded in tube 22A as shown. Alternatively, wire 36 could consist of multifilar stranded wire.

When selecting the tube 22A used with a particular drug or agent, care should be taken to ensure that the particular agent will be compatible with the material from which the inner cylindrical insulating jacket 32 is composed. The inner cylindrical insulating jacket 32 and outer cylindrical insulating jacket 30 should be sufficiently flexible to facilitate insertion. The outer cylindrical insulating jacket 30 should be biocompatible. While it is desirable to have the inner insulating jacket 32 be biocompatible it may not be absolutely necessary provided the inner insulating layer can be kept from contacting the biological tissue. An enhanced tear resistant silicone elastomer or polyurethane are examples of materials that could be used. A durometer shore value of 80 is preferred.

Tube 22A is surgically implanted through a hole in the skull 123 and catheter 22 is implanted between the skull and the scalp 125 as shown in FIG. 1. A stylet may be placed into the center of tube 22A to give it stiffness when introducing the tube into the brain. After the stylet is removed, center lumen 34 constitutes. a catheter which can be used to infuse an agent, including a drug. Catheter 22 is joined to implanted device 10 in the manner shown. Tube 22A may be continuous with tube 22 or there may be an intervening connection most likely at the burr hole or located somewhere along the subcutaneous path.

Catheter 22 may be divided into twin tubes, tube 22A and a second tube (not shown), that are implanted into the brain bilaterally. Alternatively, the second tube may be supplied with drugs from a separate catheter and pump and with electrodes from a separate signal generator.

Referring again to FIG. 1, a system or device 16 made in accordance with the preferred embodiment also may be implanted below the skin of a patient. Device 16 may take the form of a signal generator Model 7424 manufactured by Medtronic, Inc. of Minneapolis, Minn. under the trademark Itrel II.

Figure 2:
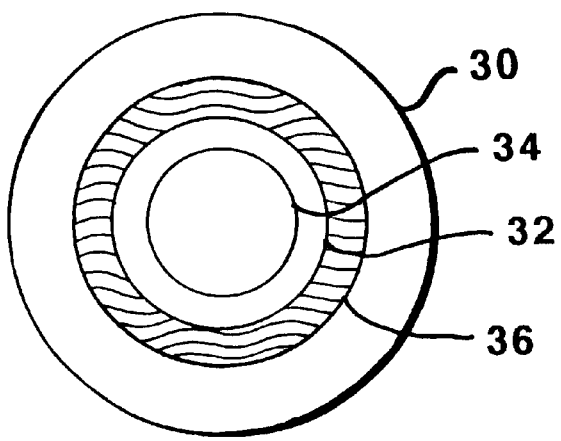
FIG. 2 is a cross-sectional view of the catheter-electrode of FIG. 1 taken along line 2—2 of FIG. 3.
Figure 3:
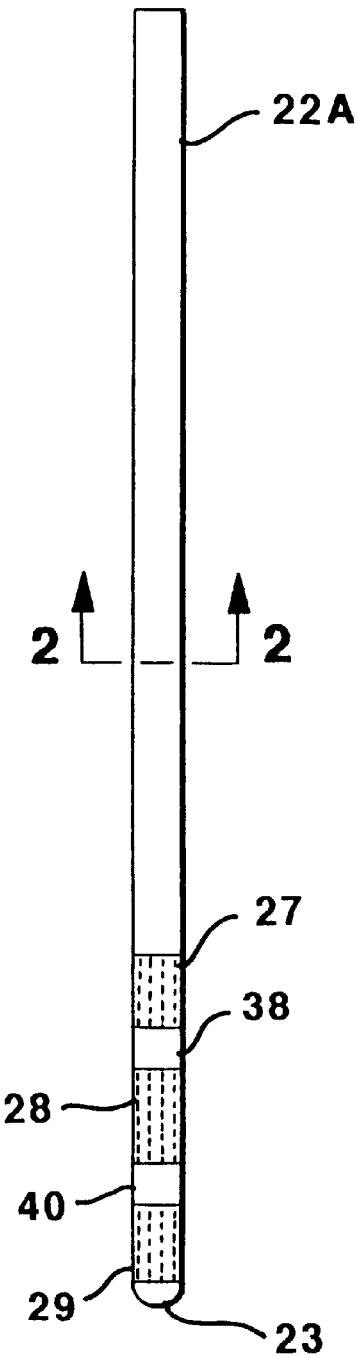
FIG. 3 is a diagrammatic view of the catheter-electrode shown in FIG. 1.

The distal end of tube 22A terminates in stimulation electrodes 38 and 40 (FIG. 3). Each of electrodes 38 and 40 is individually connected to device 16 through a conductor in wire bundle 36 (FIG. 2). The wires exit catheter 22 to form a cable 42 which is joined to implanted signal generator 16 in the manner shown in FIG. 1. While the preferred embodiment shows two electrodes on tube 22A (FIG. 3), some brain locations may require a greater number. In addition, tube 22A may have only one electrode using a portion of the case of the signal generator 16 (FIG. 1) as the reference electrode. Furthermore, in some instances infusion conduit 34 (FIG. 2) and conductor conduit 36 may not be concentric tubes but rather separate conduits located beside each other in a common tube as is embodied in FIG. 6 of U.S. Pat. No. 5,458,629 (Baudino et. al.), incorporated by reference.

Signal generator 16 is implanted in a human body, preferably in a subcutaneous pocket located over the chest cavity or the abdomen. While showed as separate devices in FIG. 1, devices 10 and 16 could be incorporated into a common device.

The present invention may preferably be implemented by providing seven different drug dosages from 0 dosage to a 1.0 ml dosage with 0.1 ml increments between choices. The time interval between dosages can preferably be selected between one and twelve hours in seven choices. This is the same type of dosage and interval described in connection with device 10 shown in the '147 Patent (column 5, beginning at line 63). The seven drug dosages and corresponding time increments may be loaded into RAM 102a (FIG. 1B of the '147 Patent). The selected dosage and interval of a drug is then delivered, as described in the '147 Patent, through catheter 22 and tube 22A to a selected location in the brain appropriate for the treatment of anxiety disorders.

The type of drugs administered by device 10 into the brain depend on the specific location at which distal end 25 of tube 22A is surgically implanted. The appropriate brain location to surgically implant distal end 25, the desired action on the neurons at that location and the types of drug agents useful at that location are provided in the following Table I:

TABLE I

| BRAIN LOCATION | DESIRED ACTION | TYPES OF AGENTS |
| --- | --- | --- |
| Anterior Limb of Internal Capsule | Decrease neuronal activity | Anesthetic |
| Nucleus Accumbens | Decrease neuronal activity | GABA Agonist |
| Cingulum fibers | Decrease neuronal activity | Anesthetic |
| Cingulate Gyrus | Decrease neuronal activity | GABA Agonist |
| Dorsal Medial Nucleus of Thalamus | Decrease neuronal activity | GABA Agonist |
| Locus Ceruleus | Decrease neuronal activity | GABA Agonist |
| Amygdyla | Decrease neuronal activity | GABA Agonist |
| Dorsal raphe Nucleus | Decrease neuronal activity | GABA Agonist |
| Septum | Decrease neuronal activity | GABA Agonist |
| Frontal Cortex | Decrease neuronal activity | Glutamate antagonist GABA Agonist |
| Anterior Thalamic Nucleus | Decrease neuronal activity | GABA Agonist |
| Mammillary body | Decrease neuronal activity | GABA Agonist |

Coordinates for the portions of the brain described in Table I are as follows:

TABLE II

| BRAIN REGION | MEDIAL-LATERAL DIMENSION | DORSAL-VENTRAL DIMENSION | ANTERIOR-POSTERIOR DIMENSION |
|---|---|---|---|
| Anterior Limb of Internal Capsule | 1.8 to 2.0 | 0.2 to −0.2 | 2.2 to 2.9 |
| Head of the Caudate Nucleus/Nucleus Accumbens | 0.5 to 2.5 | 1.0 to −1.0 | 1.5 to 3.5 |
| Cingulum fibers | 0.0 to 1.0 | 2.0 to 3.0 | 0.0 to 4.5 |
| Cingulate Gyrus | 0.0 to 1.5 | 2.0 to 3.5 | 0.0 to 4.5 |
| Dorsal Medial Nucleus of Thalamus | 0.0 to 1.0 | 0.2 to 1.7 | 0.1 to −1.1 |
| Locus Ceruleus | 0.0 to 0.5 | −1.0 to −1.7 | −1.5 to −2.0 |
| Amygdyla | 1.0 to 2.5 | −1.2 to −2.5 | 0.7 to 2.0 |
| Dorsal raphe Nucleus | 0.0 to 0.5 | −0.2 to −1.0 | −1.0 to −2.0 |
| Septum | 0.0 to 0.5 | 0.2 to 1.6 | 0.5 to 2.3 |
| Frontal Cortex | 0.0 to 5.0 | 2.0 to −2.5 | 4.0 to 7.0 |
| Anterior Thalamus | 0.2 to 1.2 | 0.2 to 1.3 | 0.5 to −0.5 |
| Mamillary body | 0.0 to 0.5 | −0.5 to 1.2 | 0.2 to 1.2 |

In the foregoing table: the medial-lateral dimensions are relative to midline of the brain; the anterior-posterior dimensions are relative to the midpoint between the anterior commissure and posterior commissure with negative indicating the posterior direction; the dorsal-ventral dimensions are relative to a line connecting the midpoints of the anterior and posterior commissures with negative being ventral to; all dimensions are in centimeters.

Alternatively, these agents might be infused into the lateral ventricle or third ventricle of the brain or just beneath the dura above the cortex or in the intrathecal space.

In this instance the drug would diffuse to the appropriate site of action.

Exemplary liquid agents which provide the desired actions identified in Table I, ranges of dosages and concentrations for the liquid agents are provided in the following Table III:

TABLE III

| DRUG CLASS | SPECIFIC DRUG | DOSING RANGE |
|---|---|---|
| Glutamate Agonist | D-Cycloserine | 1–10 muM |
| | L-AP4 | 1–10 muM |
| | Carboxyphenylglycine | 10–500 muM |
| | L-glutamic acid | 1–100 muM |
| | cis-Piperidine-2,3-dicarboxylic acid | 1–10 muM |
| | (+/−)-trans-ACPD | 1–10 muM |
| | L-AP4 | 1–10 muM |
| Glutamate Antagonists | MK801(dizocilpine) | 1–20 muM |
| | ketamine Hcl | 5–50 muM |
| | AP-3 | 1–10 muM |
| | Dextromethorpban | 1–100 muM |
| | MCPD | 0.02–10 muM |
| | dextrorphan tartrate | 1–100 muM |
| | CNQX | 1–100 muM |
| GABA Agonists | baclofen | 0.1–10 muM |
| | muscinol HBr | 100–500 muM |
| GABA Antagonists | Gabazine | 1–50 muM |
| | Saclofen | 0.5–25 muM |
| | Bicuulline | 1–100 muM |
| | picrotoxin | 10–100 muM |
| Dopamine Antagonist | (+) apomorphine Hcl | 5–20 muM |
| | spiperone Hcl | 0.1–10 muM |
| | haloperidol | 10–100 muM |
| | (−) Sulpiride | 0.05–1 muM |
| Dopamine Agonist | methanesulfonate | 1–10 muM |
| | (−) apomorphine pergolide | 10–30 muM |
| Anesthetic | Lidocaine hydrochloride | 5–20 muM |

In Table II, muM means millimicromolar.

Microprocessor 100 within device 10 can be programmed so that a controlled amount of drug described in Table III can be delivered to the specific brain sites described in Table I.

The applicant has discovered that anxiety disorders, including phobias, panic attacks, and obsessive compulsions can be treated by electrically stimulating brain tissue either alone or while drugs are being administered as described above. The stimulation can be achieved by an ITREL II signal generator implemented as signal generator 16 (FIG. 1).

Electrical stimulation of neural tissue may be implemented by providing pulses to electrodes 38 and 40 (FIG. 3) preferably having amplitudes of 0.1 to 20 volts, pulse widths varying from 0.02 to 1.5 milliseconds, and repetition rates preferably varying from 2 to 2500 Hz. Pulses with the selected characteristics are then delivered from signal generator 16 through cable 42, catheter 22, tube 22A and electrodes 38 and 40 to the targeted tissue within brain B. The appropriate stimulation pulses are generated by signal generator 16 based on the programmed values established by the clinician. The type of stimulation administered by signal generator 16 to the brain depends on the specific location at which the electrodes 38 and 40 of tube 22A are surgically implanted and the desired action on the neurons at that location. If the neuronal activity is to be blocked, signal generator 16 will be programmed with a frequency preferably in the range 50 to 2500 HZ. If the neuronal activity is to be facilitated, the stimulus frequency is chosen preferably in the range of 2 to 100 Hz.

The appropriate stimulation for use in connection with the specific locations of the brain in which tube 22A terminates, together with the effect of the stimulation on that portion of the brain for an anxiety disorder is provided in the following Table IV:

TABLE IV

| BRAIN LOCATION | DESIRED ACTION | TYPES OF STIMULATION |
|---|---|---|
| Anterior Limb of Internal Capsule | Decrease Neuronal activity | High Frequency |
| Head of the Caudate Nucleus / Nucleus Accumbens | Decrease Neuronal activity | High Frequency |
| Cingulum fibers | Decrease Neuronal activity | High Frequency |
| Cingulate Gyrus | Decrease Neuronal activity | High Frequency |
| Dorsal Medial Nucleus of Thalamus | Decrease Neuronal activity | High Frequency |
| Locus Ceruleus | Decrease Neuronal activity | High Frequency |
| Amygdyla | Decrease Neuronal activity | High Frequency |
| Dorsal raphe Nucleus | Decrease Neuronal activity | High Frequency |
| Septum | Decrease Neuronal activity | High Frequency |

TABLE IV-continued

| BRAIN LOCATION | DESIRED ACTION | TYPES OF STIMULATION |
|---|---|---|
| Frontal Cortex | Decrease Neuronal activity | High Frequency |
| Anterior Nucleus of Thalamus | Decrease Neuronal activity | High Frequency |
| Mammillary body | Decrease Neuronal activity | High Frequency |

Coordinates for the portions of the brain described in Table IV are found in Table II.

A microprocessor within signal generator 16 can be programmed so that the desired stimulation can be delivered to the specific brain sites described in Table II.

The system shown in FIG. 1 is an open-loop system. The microcomputer algorithm programmed by the clinician sets the stimulation parameters of signal generator 16 and/or infusion rates of infusion pump 10. This algorithm may change the parameter values over time but does so independent of any changes in symptoms the patient may be experiencing. Alternatively, the closed-loop systems show in FIGS. 4–7 which incorporate sensor 130 to provide feedback could be used to provide enhanced results.

Figure 4:
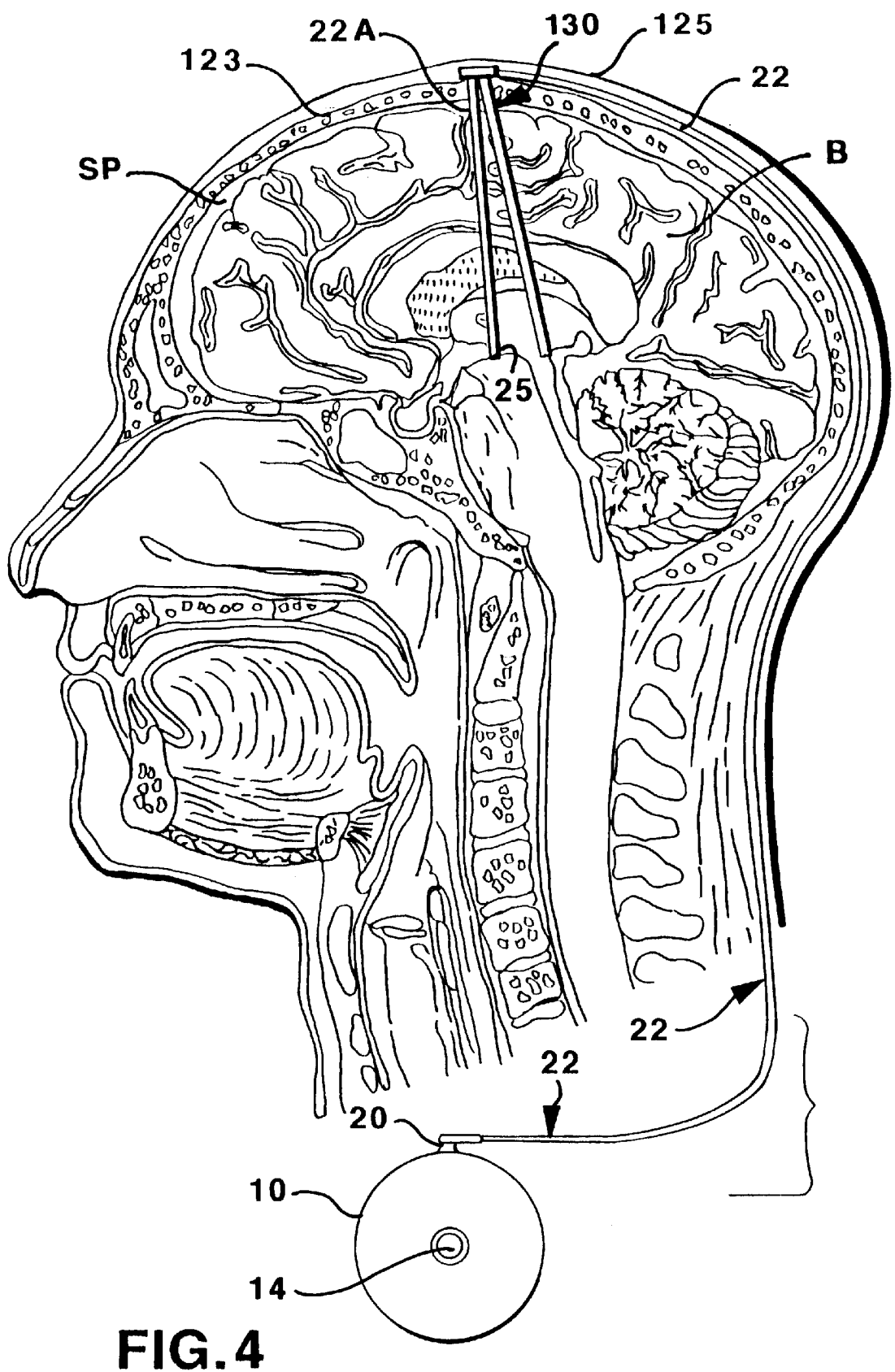
FIG. 4 is a diagrammatic illustration of a catheter and a sensor implanted in a brain and a pump coupled to the catheter and sensor.
Figure 5:
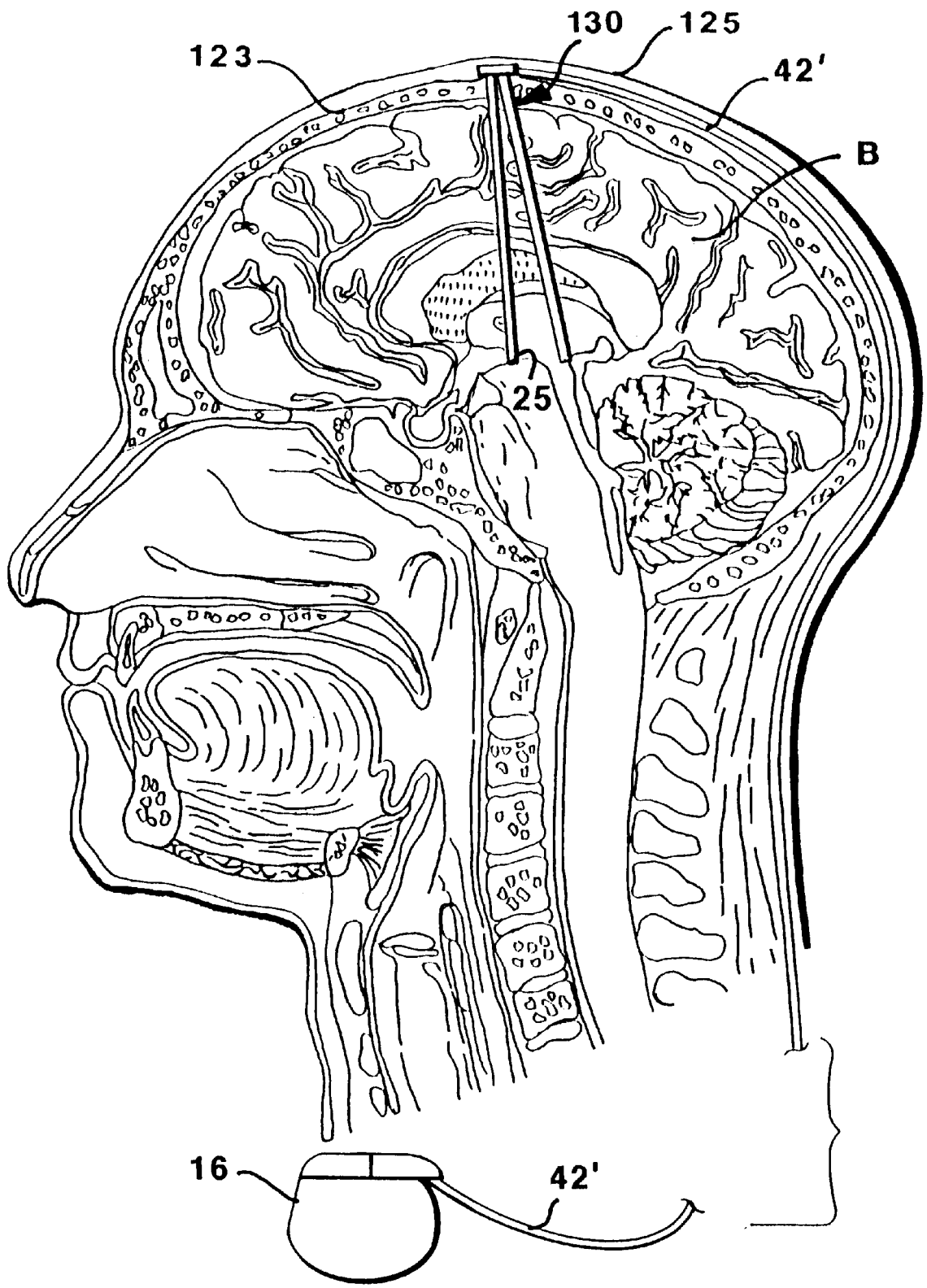
FIG. 5 is a diagrammatic illustration of a lead and a sensor implanted in a brain and a signal generator coupled to the lead and sensor.

FIG. 4 depicts an infusion pump 10 connected through tube 22 to a distal portion 22A and a separate sensor portion 130. FIG. 5 depicts a signal generator 16 connected through cable 42' which has a distal portion 42'A with electrodes 38 and 40 located at the distal end and a sensor portion 130. The devices in FIGS. 4 and 5 provide "closed-loop" infusion of medication and "closed-loop" stimulation respectively.

Figure 6:
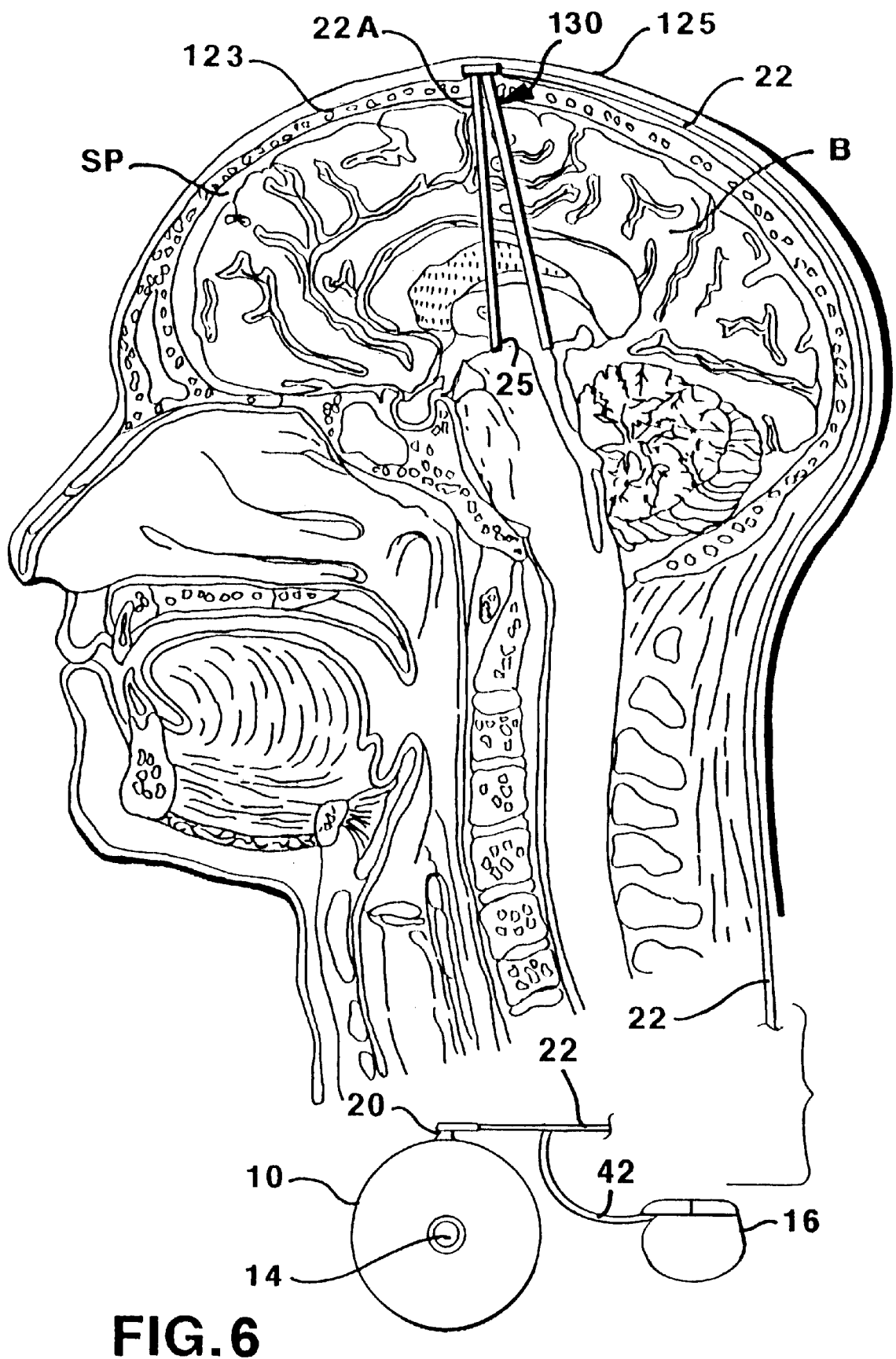
FIG. 6 is a diagrammatic illustration of a combined lead and catheter and a sensor implanted in a brain and a signal generator and pump coupled to the combined catheter and electrode and sensor.

Alternatively, the device in FIG. 6 allows for the combination of infusion and stimulation both therapies being controlled by a feed back sensor 130. In FIG. 6, the stimulation electrodes 38 and 40 are made a part of tube 22A as depicted in FIG. 3.

Figure 7:
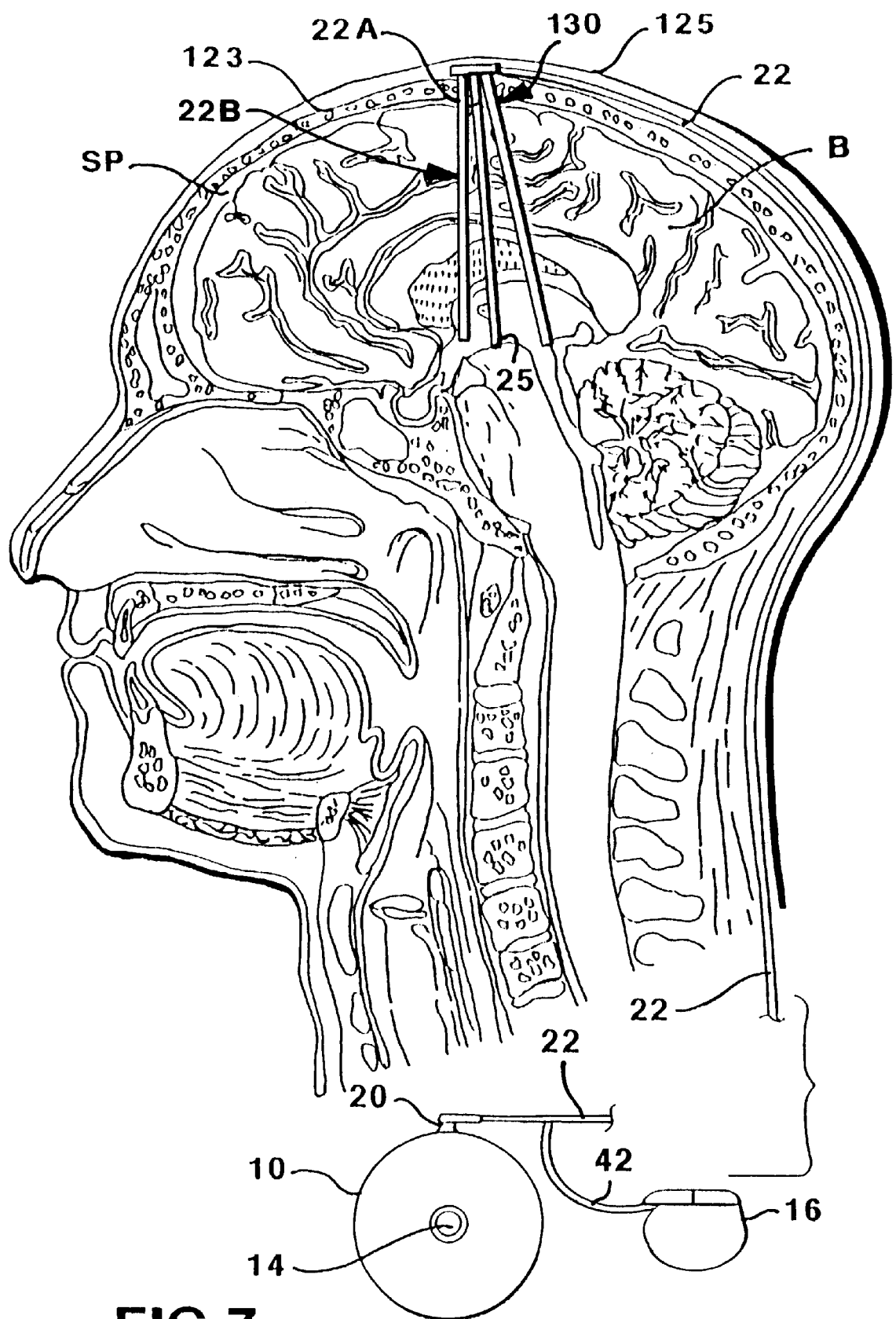
FIG. 7 is a diagrammatic illustration of a separate lead and catheter and a sensor implanted in a brain and a signal generator and pump coupled to the lead, catheter and sensor.

Alternatively, referring to FIG. 7 the stimulation electrodes 38 and 40 could be located on a separate tube 22B away from the microporous regions 27–29 located on tube 22A. This would allow delivery of stimulation to a different site in brain B than the site where medication is delivered. The sensor 130 is located at still a different site in brain B. Under certain circumstances it may be desirable to have sensor 130 physically located on either tube 22A or tube 22B.

A sensor 130 is implanted into a portion of a patient's body suitable for detecting symptoms of the disorder being treated. Sensor 130 is adapted to sense an attribute of the symptom to be controlled or an important related symptom. For anxiety disorders it is desirable to sense a physiological symptom of a heightened state of arousal or anxiety. Physiological signals related to heart rate or respiration rate, blood gases, galvanic skin response or muscle tension could provide feedback to adjust stimulation or infusion parameters.

Sensor 130 may detect the electrocardiogram through electrodes outside the brain near the heart. Alternatively, electrodes located within Brain B and adjacent a small vessel may be used to detect features of the heart rate.

Sensor 130 may detect muscle EMG in one, two or more muscles, or in reciprocal muscles at one joint. For such detection, sensor 130 may take the form of a lead with one or more recording electrodes inserted into the muscle of interest.

Brain EEG (e.g., cortical potentials recorded above the neurons controlling specific aspects of behavior associated with the neurological disorder) also may be detected by sensor 130. In this case, sensor 130 would take the form of an electrode with impedance values preferably chosen to optimize recording of electrical signals.

Yet another form of sensor 130 would include a device capable of detecting nerve compound action potentials (e.g., either sensory afferent information from muscle or skin receptors or efferent motor potentials controlling a muscle of interest).

Sensor 130 also may take the form of a device capable of detecting nerve cell or axon activity that is related to the pathways at the cause of the symptom, or that reflects sensations which are elicited by the symptom. Such a sensor may be located deep in the brain. For such detecting, sensor 130 may take the form of an electrode inserted into the internal capsule, motor cortex or basal ganglia of the brain. Signals of any kind that are received by the sensor may by amplified before transmission to circuitry contained within device 10 or device 16.

Sensor 130 may take the form of a transducer consisting of an electrode with an ion selective coating applied which is capable of directly transducing the amount of a particular transmitter substance or its breakdown by-products found in the interstitial space of a region of the brain such as the ventral lateral thalamus. The level of the interstitial transmitter substance is an indicator of the relative activity of the brain region. An example of this type of transducer is described in the paper "Multichannel semiconductor-based electrodes for in vivo electrochemical and electrophysiological studies in rat CNS" by Craig G. van Horne, Spencer Bement, Barry J. Hoffer, and Greg A. Gerhardt, published in *Neuroscience Letters*, 120 (1990) 249–252.

Sensor 130 may be external to the body communicating with the implanted portions through telemetry. An example of an external sensor is an electrical device that includes an electrode attached to the surface of the skin which passes a small current to measure the skin impedance. An example of this type of sensor is described in the paper "Skin Impedance in Relation to Pain Threshold Testing by Electrical Means", by Emily E. Mueller, Robert Loeffel and Sedgwick Mead, published in J. Applied Physiology 5, 746–752, 1953. A decrease in skin impedance may indicate an increase in anxiety.

Figure 8:
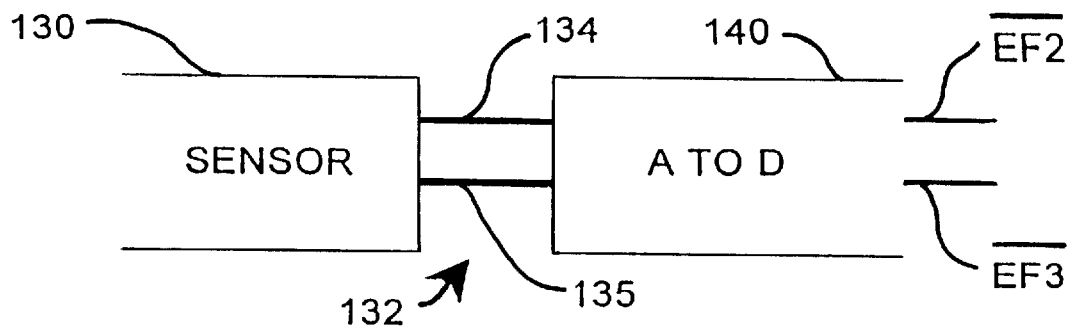
FIG. 8 is a schematic block diagram of a sensor and analog to digital converter circuit used in the preferred embodiment of the invention.
Figure 9:
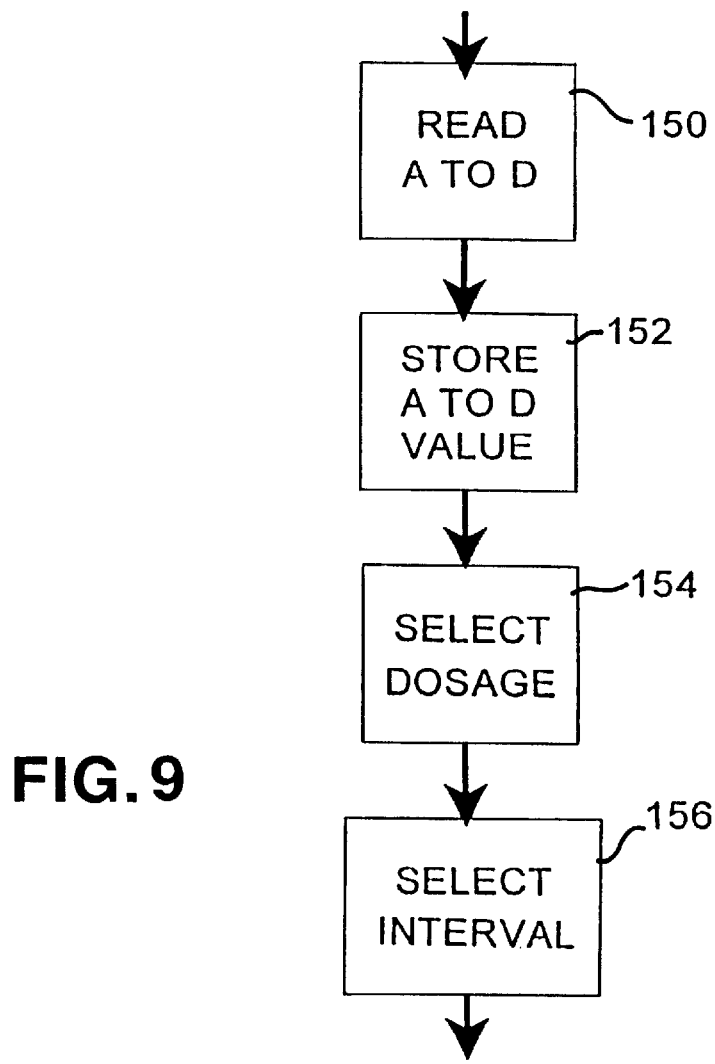
FIG. 9 is a flow chart illustrating a preferred form of a microprocessor program for utilizing the sensor to control drug dosage administered to the brain.

Other sensors such as Carbon dioxide gas sensors or other sensors that can detect the physiological parameters such as those listed above will be clear to those skilled in the art. Referring to FIG. 8, the output of sensor 130 is coupled by a cable 132 comprising conductors 134 and 135 to the input of analog to digital converter 140. Alternatively, the output of an external feedback sensor would communicate with the implanted pulse generator or pump through a telemetry downlink. The output of the analog to digital converter is connected to terminals EF2 BAR and EF3 BAR shown in FIG. 11A of U.S. Pat. No. 4,692,147 ("'147 Patent"). Before converter 140 is connected to the terminals, the demodulator 101 currently shown in FIG. 11A would be disconnected. A drug can be delivered essentially continuously (within the constraints of the particular delivery device being used) or it may be delivered during intermittent intervals coordinated to reflect the half-life of the particular agent being infused or with circadian rhythms. As an example, the symptoms of the neurological disorder may normally subside at night when the person is sleeping so the drug delivery rates might be reduced to coincide with the hours between 10 p.m. and 7 a.m.

Microprocessor 100 within device 10 can be programmed so that a controlled amount of drug can be delivered to the specific brain sites described in Table I. Alternatively, sensor 130 can be used with a closed loop feedback system in order to automatically determine the level of drug delivery necessary to alleviate the symptoms of the neurological disorder.

Figure 10:
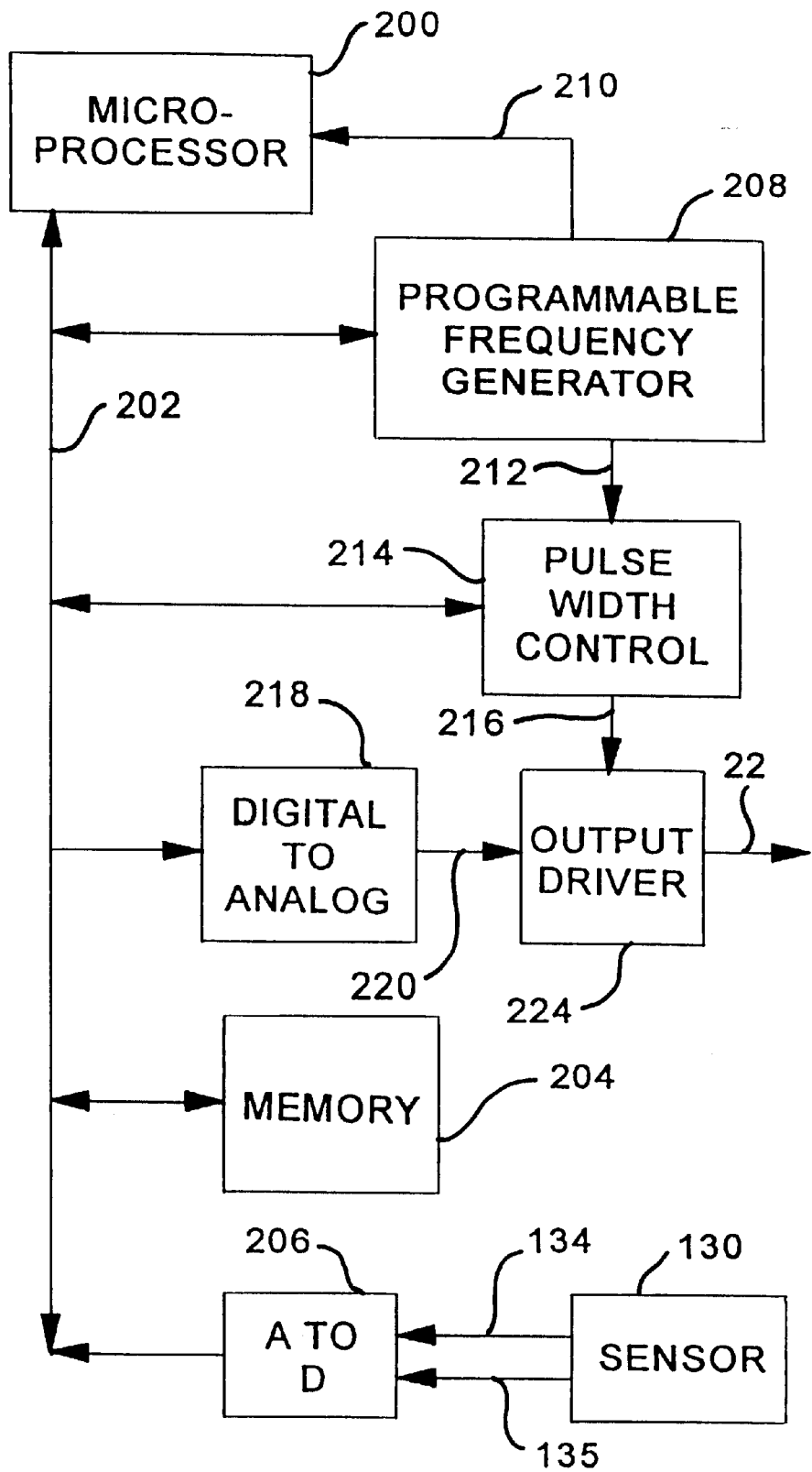
FIG. 10 is a schematic block diagram of a microprocessor and related circuitry for utilizing the sensor to control stimulation administered to the brain.

The applicants have discovered that the efficacy of treatment may be enhanced if the neural tissue is stimulated while drugs are being administered as described above. The stimulation can be achieved by a modified form of the ITREL II signal generator implemented as signal generator 16 (FIG. 1) which is described in FIG. 10. The output of sensor 130 is coupled by cable 132, comprising conductors 134 and 135, to the input of an analog to digital converter 206. Alternatively, the output of an external sensor would communicate with the implanted pulse generator through a telemetry downlink.

For some types of sensors, a microprocessor and analog to digital converter will not be necessary. The output from sensor 130 can be filtered by an appropriate electronic filter in order to provide a control signal for signal generator 16. An example of such a filter is found in U.S. Pat. No. 5,259,387 "Muscle Artifact Filter, Issued to Victor de Pinto on Nov. 9, 1993.

The output of the analog to digital converter 206 is connected to a microprocessor 200 through a peripheral bus 202 including address, data and control lines. Microprocessor 200 processes the sensor data in different ways depending on the type of transducer in use. When the signal on sensor 130 exceeds a level programmed by the clinician and stored in a memory 204, increasing amounts of stimulation will be applied through an output driver 224.

The stimulus pulse frequency is controlled by programming a value to a programmable frequency generator 208 using bus 202. The programmable frequency generator provides an interrupt signal to microprocessor 200 through an interrupt line 210 when each stimulus pulse is to be generated. The frequency generator may be implemented by model CDP1878 sold by Harris Corporation.

The amplitude for each stimulus pulse is programmed to a digital to analog converter 218 using bus 202. The analog output is conveyed through a conductor 220 to an output driver circuit 224 to control stimulus amplitude.

Microprocessor 200 also programs a pulse width control module 214 using bus 202. The pulse width control provides an enabling pulse of duration equal to the pulse width via a conductor. Pulses with the selected characteristics are then delivered from signal generator 16 through cable 22 and lead 22A or 22B to the target locations of a brain B.

Microprocessor 200 executes an algorithm shown in FIGS. 11–15 in order to provide stimulation with closed loop feedback control. At the time the stimulation signal generator 16 or alternative device in which the stimulation and infusion functions are combined is implanted, the clinician programs certain key parameters into the memory of the implanted device via telemetry. These parameters may be updated subsequently as needed. Step 400 in FIG. 11 indicates the process of first choosing whether the neural activity at the stimulation site is to be blocked or facilitated (step 400(1)) and whether the sensor location is one for which an increase in the neural activity at that location is equivalent to an increase in neural activity at the stimulation target or vice versa (step 400(2)). Next the clinician must program the range of values for pulse width (step 400(3)), amplitude (step 400(4)) and frequency (step 400(5)) which signal generator 16 may use to optimize the therapy. The clinician may also choose the order in which the parameter changes are made (step 400(6)). Alternatively, the clinician may elect to use default values.

Figure 11:
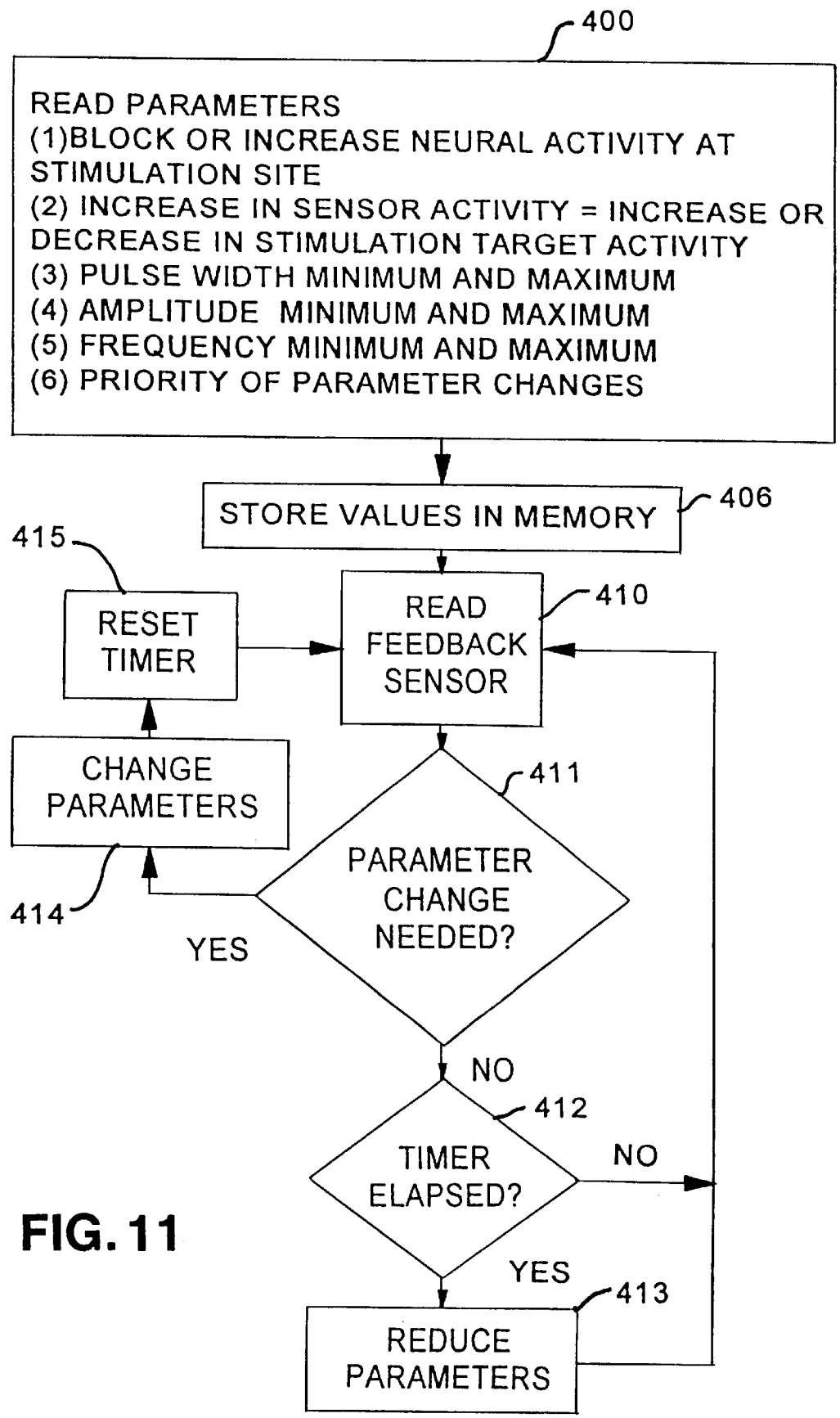
FIGS. 11–15 are flow charts illustrating a preferred form of microprocessor program for generating stimulation pulses to be administered to the brain.

The algorithm for selecting parameters is different depending on whether the clinician has chosen to block the neural activity at the stimulation target or facilitate the neural activity. FIG. 11 details steps of the algorithm to make parameter changes.

Figure 12:
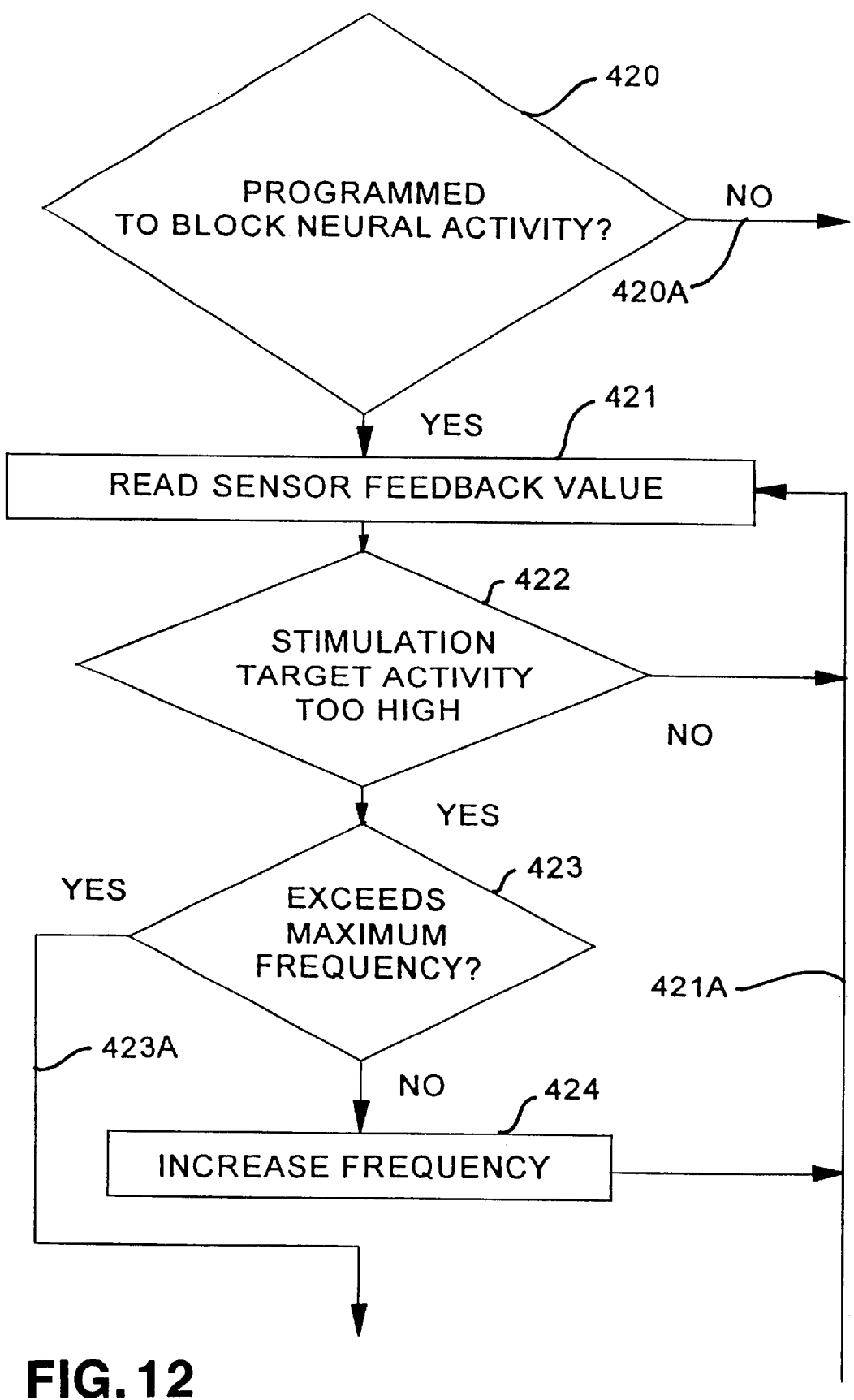
Figure 13:
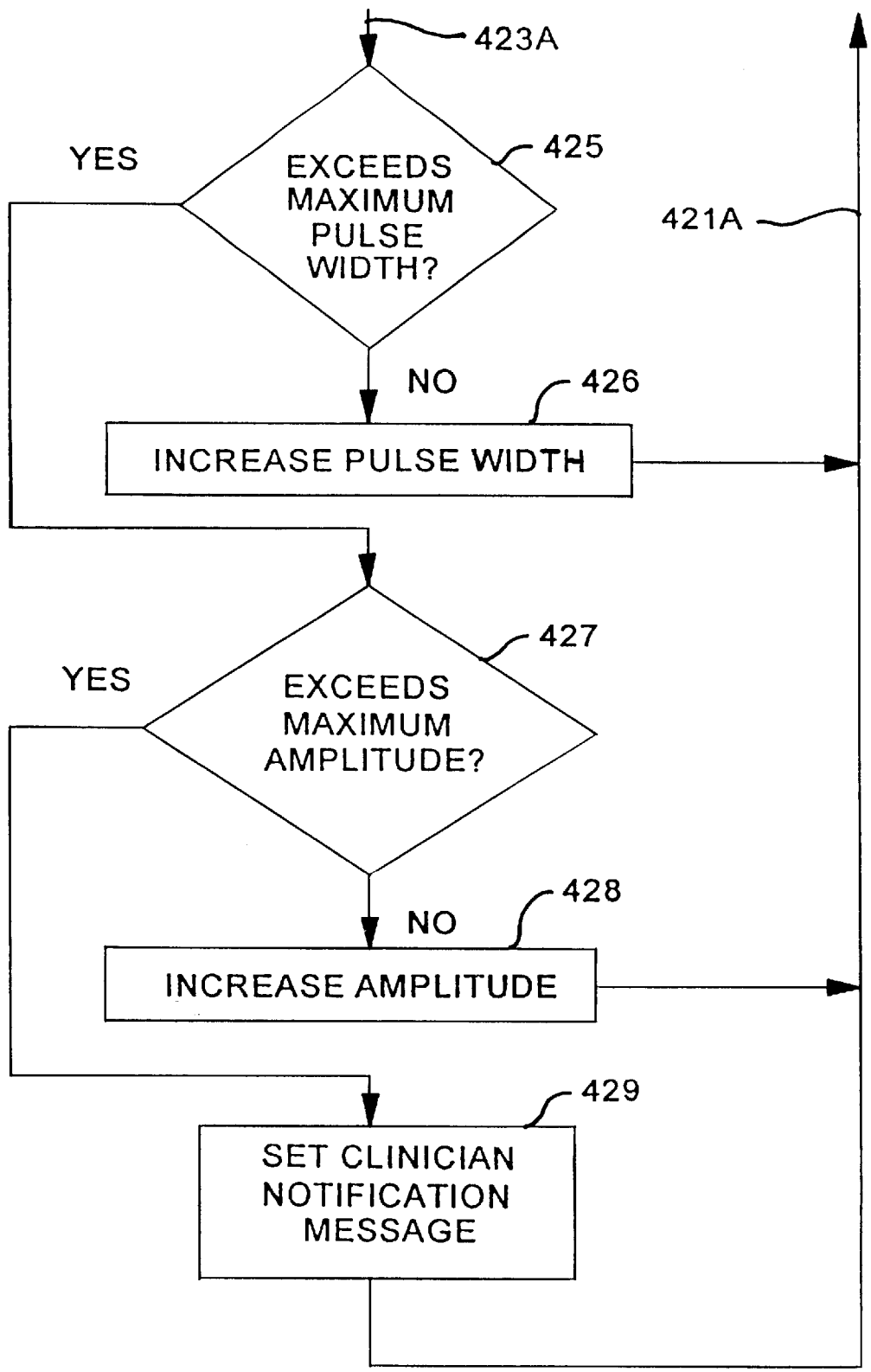
Figure 14:
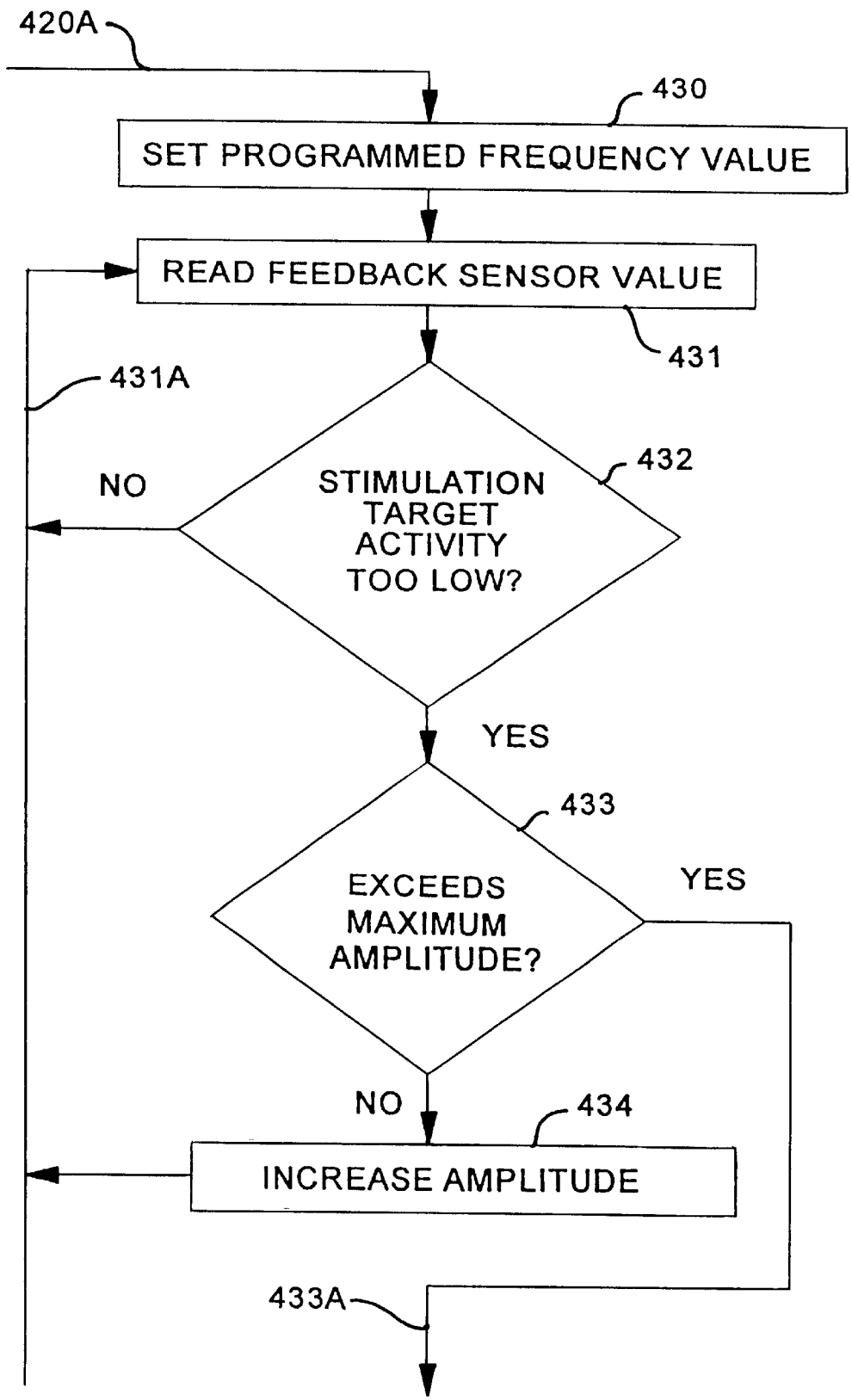

The algorithm uses the clinician programmed indication of whether the neurons at the particular location of the stimulating electrode are to be facilitated or blocked in order to decide which path of the parameter selection algorithm to follow (step 420, FIG. 12). If the neuronal activity is to be blocked, signal generator 16 first reads the feedback sensor 130 in step 421. If the sensor values indicate the activity in the neurons is too high (step 422), the algorithm in this embodiment first increases the frequency of stimulation in step 424 provided this increase does not exceed the preset maximum value set by the physician. Step 423 checks for this condition. If the frequency parameter is not at the maximum, the algorithm returns to step 421 through path 421A to monitor the feed back signal from sensor 130.

If the frequency parameter is at the maximum, the algorithm next increases the pulse width in step 426 (FIG. 13), again with the restriction that this parameter has not exceeded the maximum value as checked for in step 425 through path 423A. Not having reached maximum pulse width, the algorithm returns to step 421 to monitor the feedback signal from sensor 130. Should the maximum pulse width have been reached, the algorithm next increases amplitude in a like manner as shown in steps 427 and 428. In the event that all parameters reach the maximum, a notification message is set in step 429 to be sent by telemetry to the clinician indicating that device 16 is unable to reduce neural activity to the desired level.

Figure 15:
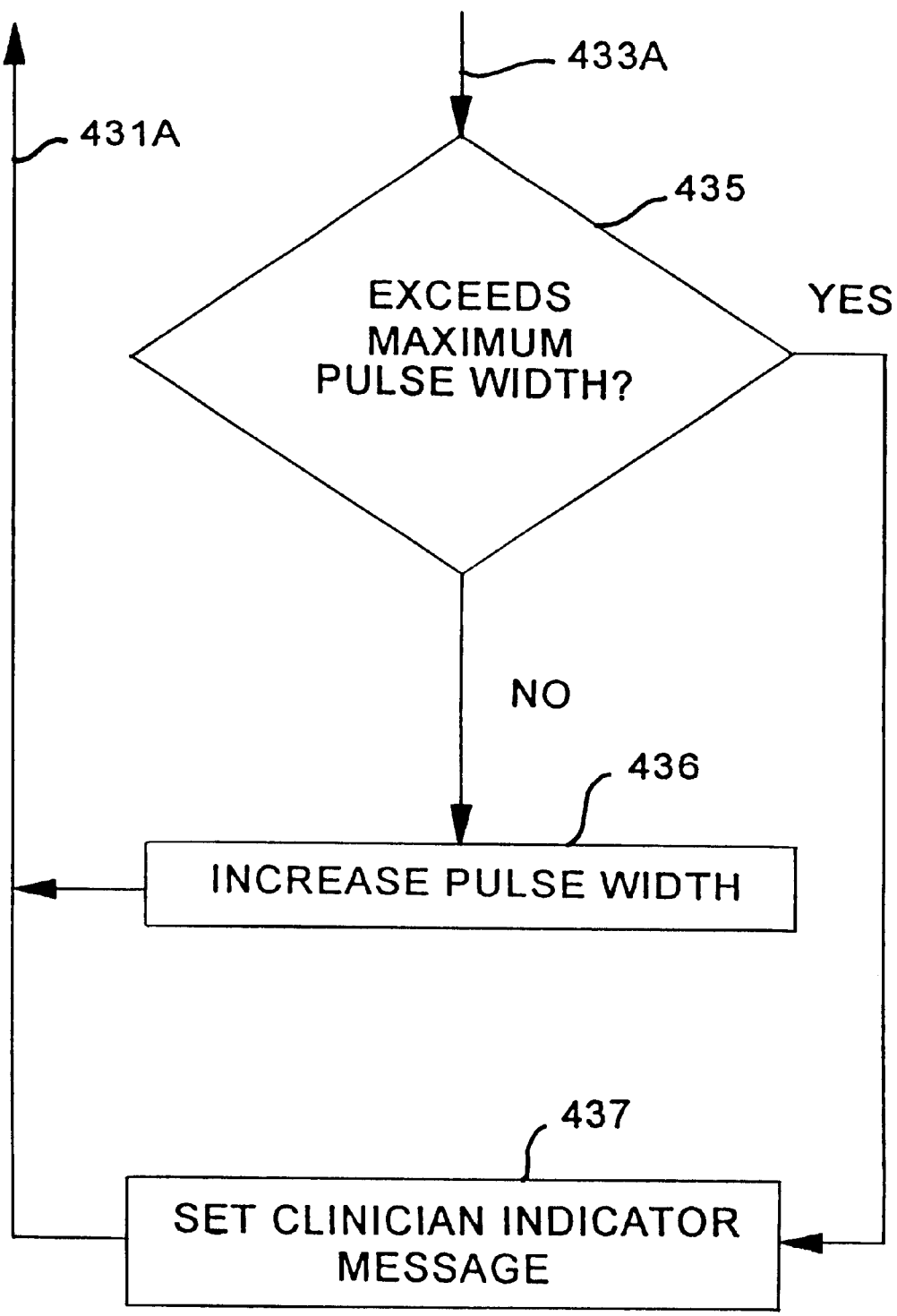

If, on the other hand, the stimulation electrode is placed in a location which the clinician would like to activate in order to alter the symptoms of the neurological disorder, the algorithm would follow a different sequence of events. In the preferred embodiment, the frequency parameter would be fixed at a value chosen by the clinician to facilitate neuronal activity in step 430 (FIG. 14) through path 420A. In steps 431 and 432 the algorithm uses the values of the feedback sensor to determine if neuronal activity is being adequately controlled. In this case, inadequate control indicates that the neuronal activity of the stimulation target is too low. Neuronal activity is increased by first increasing stimulation amplitude (step 434) provided it doesn't exceed the programmed maximum value checked for in step 433. When maximum amplitude is reached, the algorithm increases pulse width to its maximum value in steps 435 and 436 (FIG. 15). A lack of adequate alteration of the symptoms of the neurological disorder, even though maximum parameters are used, is indicated to the clinician in step 437. After steps 434, 436 and 437, the algorithm returns to step 431 through path 431A, and the feedback sensor again is read.

It is desirable to reduce parameter values to the minimum level needed to establish the appropriate level of neuronal activity in, for example, the target brain nucleus. Superimposed on the algorithm just described is an additional algorithm to readjust all the parameter levels downward as far as possible. In FIG. 11, steps 410 through 415 constitute the method to do this. When parameters are changed, a timer is reset in step 415. If there is no need to change any stimulus parameters before the timer has counted out, then it may be possible due to changes in neuronal activity to reduce the parameter values and still maintain appropriate levels of neuronal activity in the target neurons. At the end of the programmed time interval, signal generator 16 tries reducing a parameter in step 413 to determine if control is maintained.

If it is, the various parameter values will be ratcheted down until such time as the sensor values again indicate a need to increase them. While the algorithms in FIGS. 11–15 follow the order of parameter selection indicated, other sequences may be programmed by the clinician.

Figure 17:
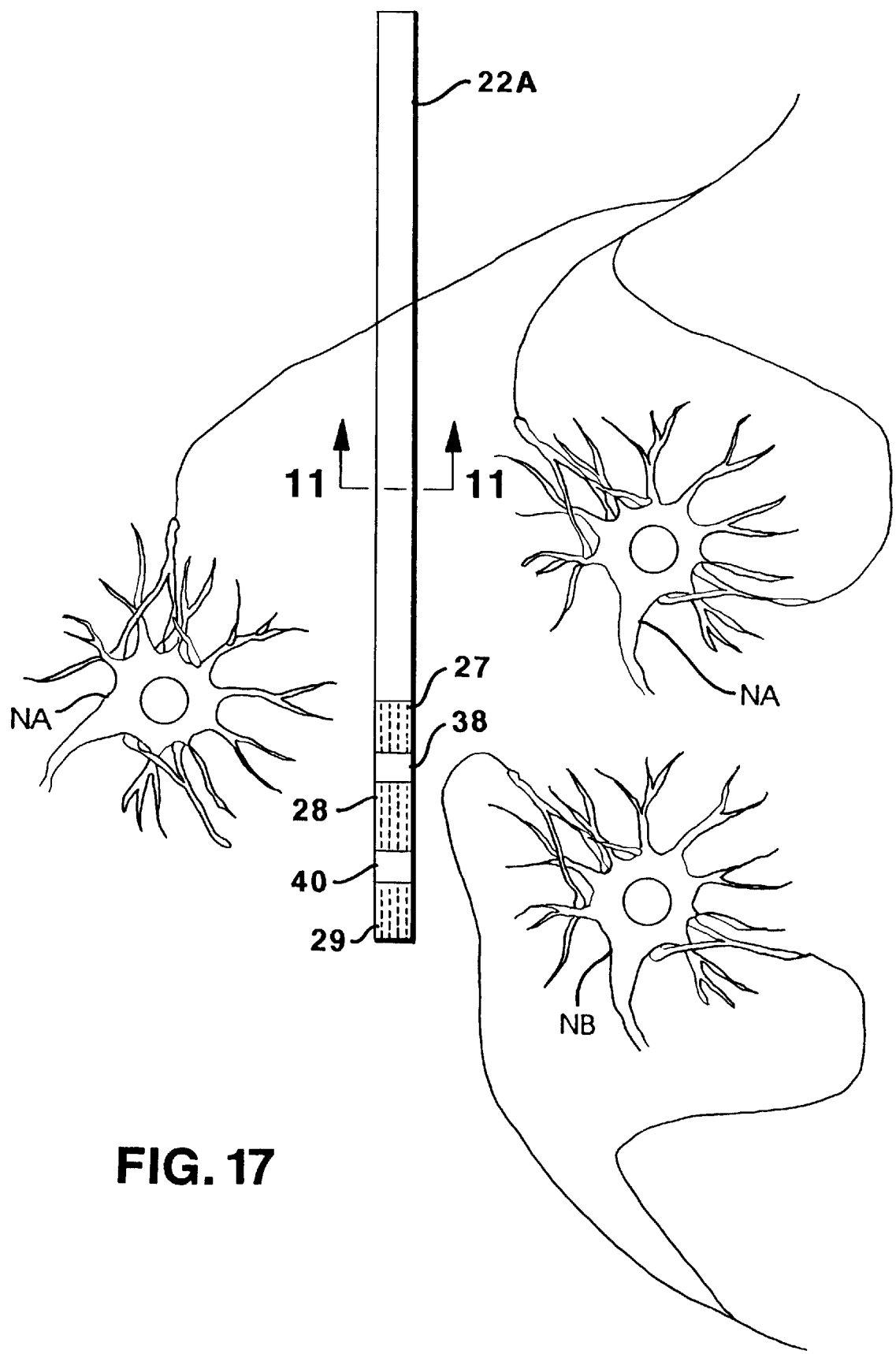
FIGS. 17–21 are diagrammatical views of the catheter-electrode shown in FIG. 1 arranged adjacent various types of neural tissue.

The foregoing techniques for simultaneous drug infusion and electrical stimulation can be applied to neural tissue in general, and are not limited to the previously described locations in the brain. FIG. 17 describes one such application in which type A neurons, such as NA, are located in the same region as type B neurons, such as NB which can typically be found in a brain. By infusing various agents through portions 27–29, neurons NA can be inhibited or excited with respect to their response to electrical stimulation provided by electrodes 38 and 40, while neurons NB remain unchanged with respect to their response to such stimulation. Thus, neurons NA or NB can be selectively stimulated by electrodes 38 and 40 due to the infusion of substances through portions 27–29 of tube 22A.

Figure 18:
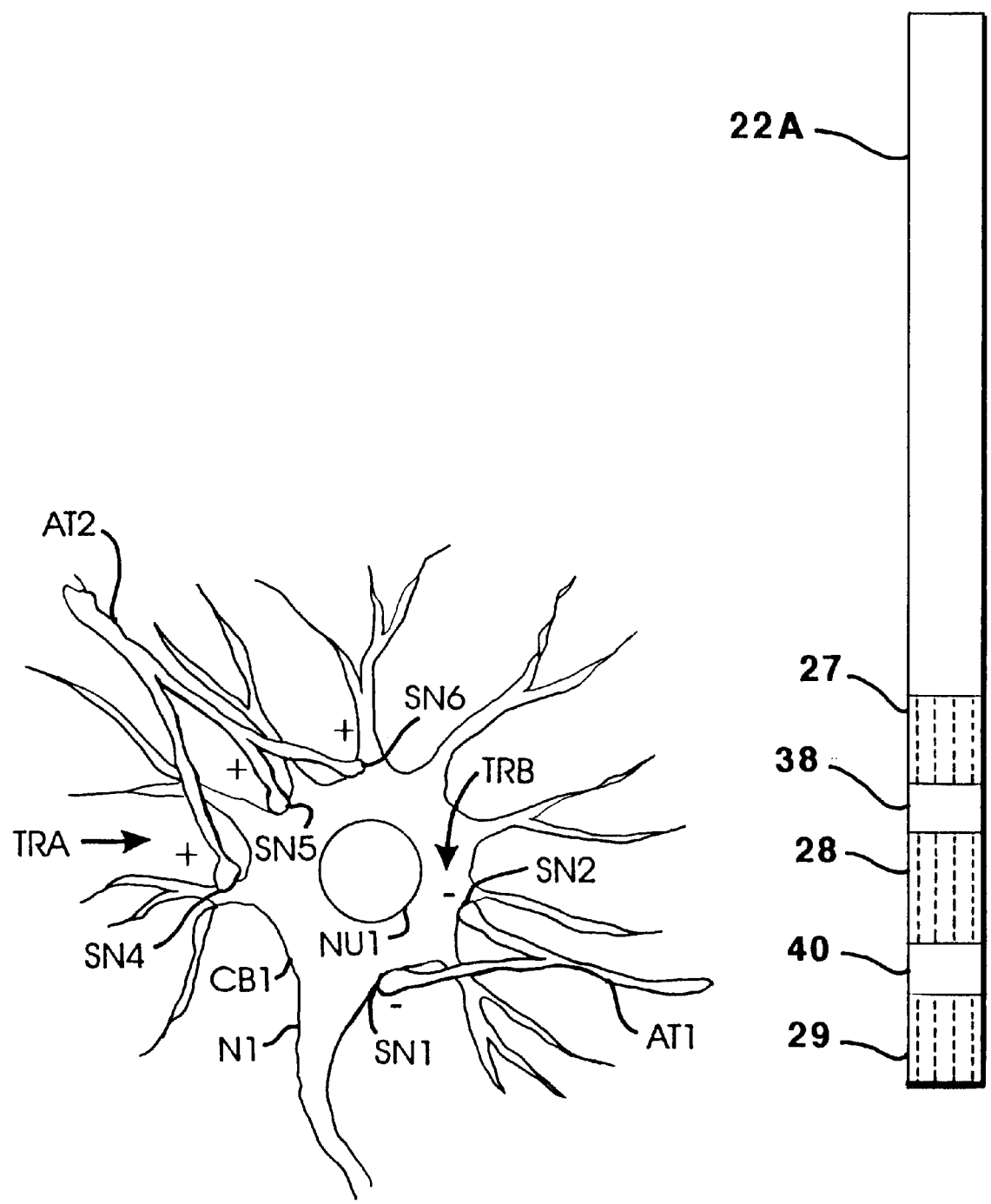

Referring to FIG. 18, a neuron N1 found in a brain has a cell body CB1 and a nucleus NU1. Neuron N1 can be excited by axon terminals AT1 at synapses SN1–SN2 by an inhibitory neurotransmitter TRB and can be excited by axon terminals AT2 at synapses SN4–SN6 by an excitatory neurotransmitter TRA. Portions 27–29 are used to infuse into the region of neuron N1 one or more of the following agents: an antagonist of transmitter TRB, an agonist of transmitter TRA, an agent to block the reuptake of transmitter TRA, a degradative enzyme for transmitter TRB and potassium. The agents can be infused separately or together in a cocktail. Such infusion leads to partial depolarization of neuron N1 and to a reduced threshold to stimulation by electrodes 38 and 40. That is, after infusion, the amplitude of stimulation required to create action potentials in neuron N1 is reduced compared to the time period before infusion.

Figure 19:
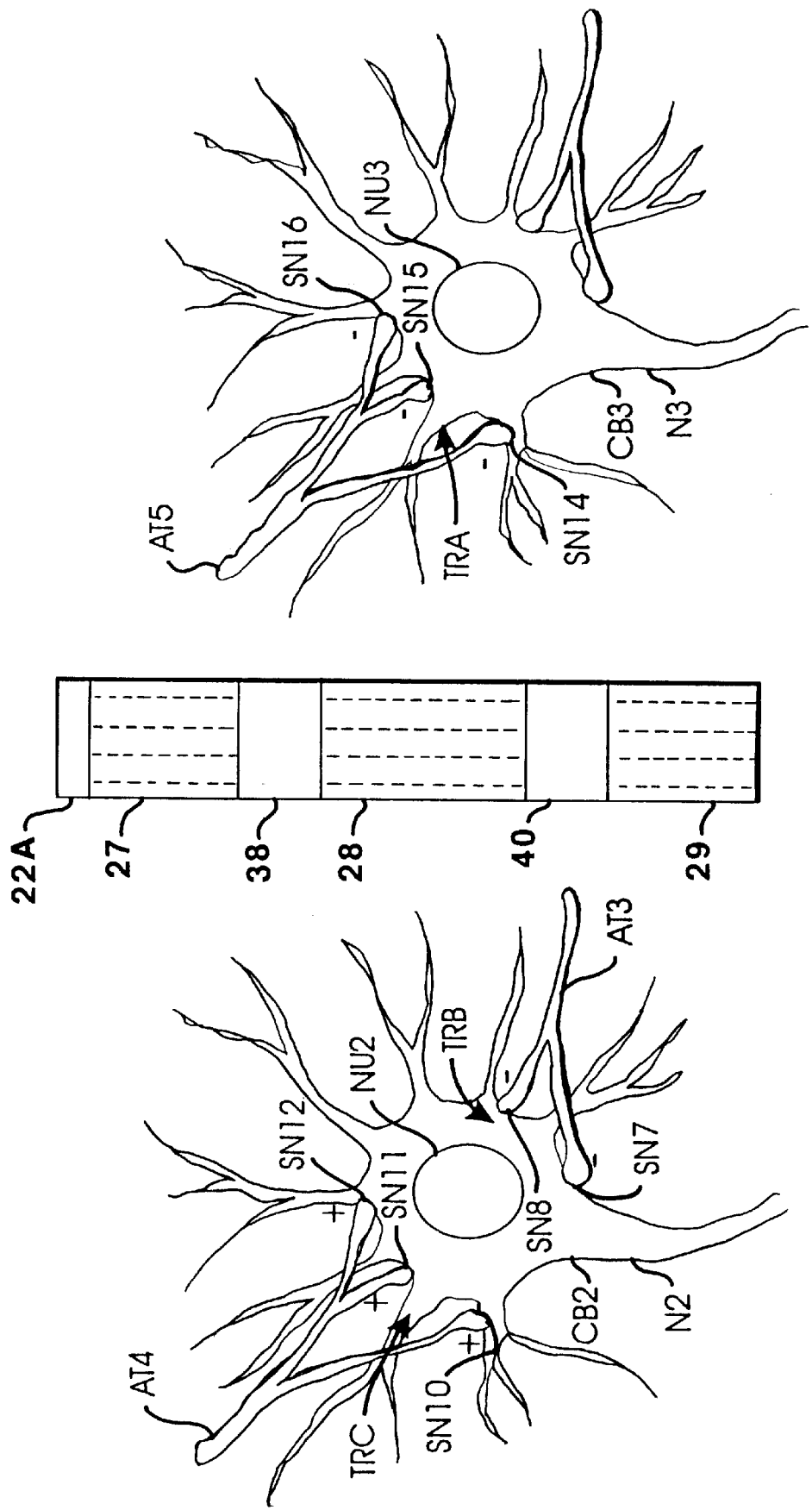

Referring to FIG. 19, a neuron N2 found in a brain has a cell body CB2 and a nucleus NU2. Neuron N2 can be inhibited by axon terminals AT3 at synapses SN7–SN8 by an inhibitory neurotransmitter TRB and can be excited by axon terminals AT4 at synapses SN10–SN12 by an excitatory neurotransmitter TRC.

A neuron N3 found in a brain has a cell body CB3 and a nucleus NU3. Neuron N3 can be inhibited by axon terminals AT5 at synapses SN14–SN16 by an inhibitory neurotransmitter TRA. Portions 27–29 of tube 22A are used to infuse into the region of neurons N2 and N3 one or more of the following agents: an agonist of transmitter TRA, an agent to block the reuptake of transmitter TRA or an agent to block a degradative enzyme for transmitter TRA. Each of these agents hyperpolarize neuron N3 and increase the potential threshold required to create action potentials in neuron N3. Therefore, neuron N2 can be selectively activated by electrodes 38 and 40 so that an action potential is created in neuron N2 without creating an action potential in neuron N3.

Selective activation of neuron N2 also can be achieved by infusing into the region of neurons N2 and N3 one or more of the following agents: an agonist for transmitter TRC, an agent to block the reuptake of transmitter TRC, an agent to block the degrading enzyme for transmitter TRC, an antagonist for transmitter TRB, an agent to enhance the reuptake of transmitter TRB or a degrading enzyme for transmitter TRB. The agents can be infused separately or together in a cocktail. Such infusion leads to partial depolarization of neuron N2 and to a reduced threshold to stimulation by electrodes 38 and 40. That is, after infusion, the amplitude of stimulation required to create action potentials in neuron N2 is reduced compared to the time period before infusion, making it easier to electrically stimulate neuron N2 relative to neuron N3.

Figure 20:
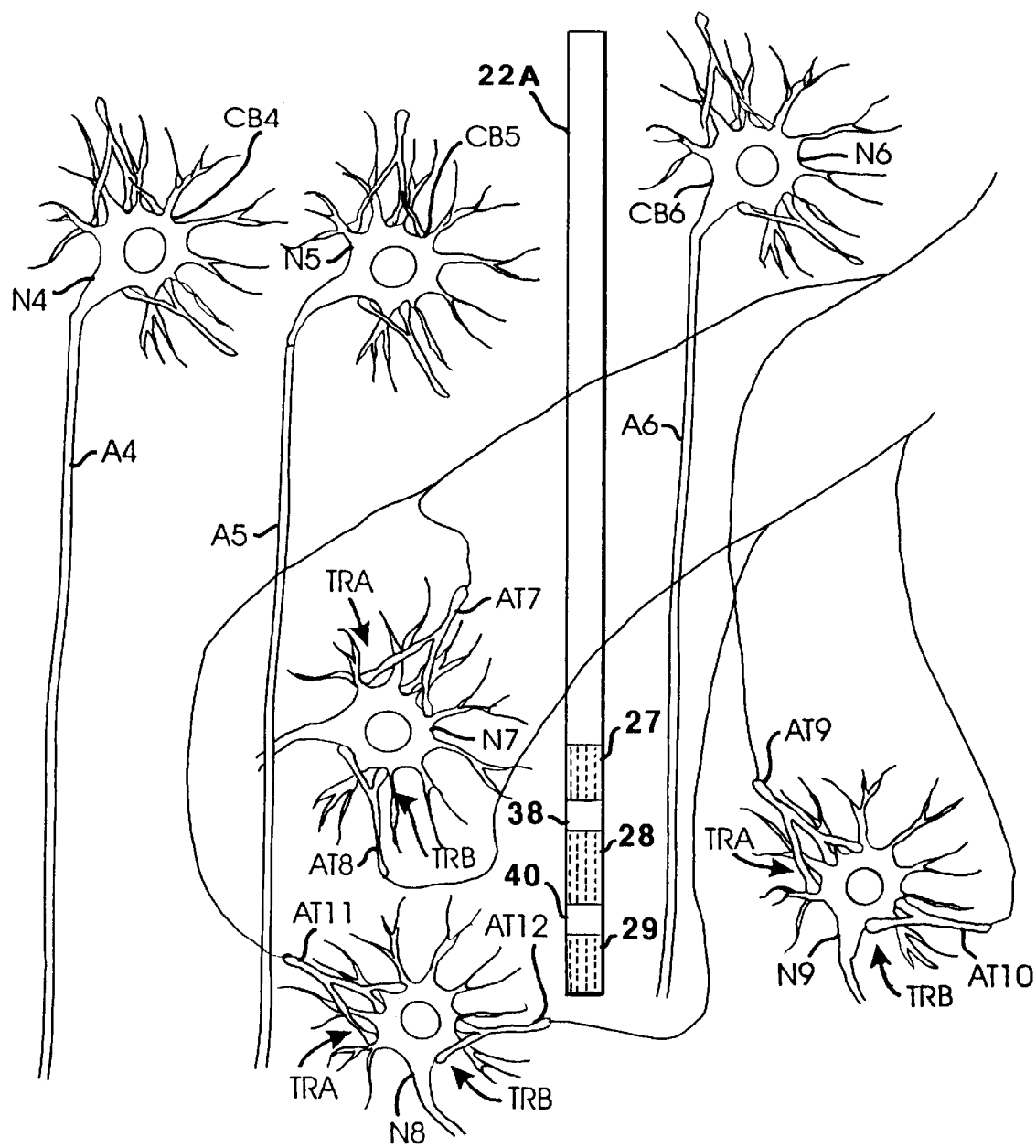

Referring to FIG. 20, neurons N4–N6 found in a brain have cells bodies CB4–CB6, respectively, and axons A4–A6, respectively, which are long fibers of passage that typically pass through white tissue in the spinal cord or brain. Cell bodies CB4–CB6 are located at portions of the body somewhat remote from infusion portions 27–29 and electrodes 38 and 40. However, portions of axons A4–A6 pass in the region of infusion portions 27–29 and electrodes 38 and 40. Neurons N7–N9 have cell bodies that are located in the region of infusion portions 27–29 and electrodes 38 and 40. Neuron N7 can be inhibited at axon terminals AT7 by an inhibitory neurotransmitter TRA and excited at axon terminals AT8 by an excitatory neurotransmitter TRB; neuron N9 can be inhibited at axon terminals AT9 by inhibitory neurotransmitter TRA and excited at axon terminals AT10 by excitatory neurotransmitter TRB; and neuron N8 can be inhibited at axon terminals AT11 by inhibitory neurotransmitter TRA and excited at axon terminals AT12 by an excitatory neurotransmitter TRB. Portions 27–29 are used to infuse an agonist of transmitter TRA, a reuptake blocker to transmitter TRA, a degrading enzyme blocker to transmitter TRA or an antagonist or degrading enzyme to transmitter TRB to raise the stimulation threshold of neurons N7–N9. Neurons N4–N6 are not affected by the infusion and can be selectively activated by stimulation supplied by electrodes 38 and 40.

Figure 21:
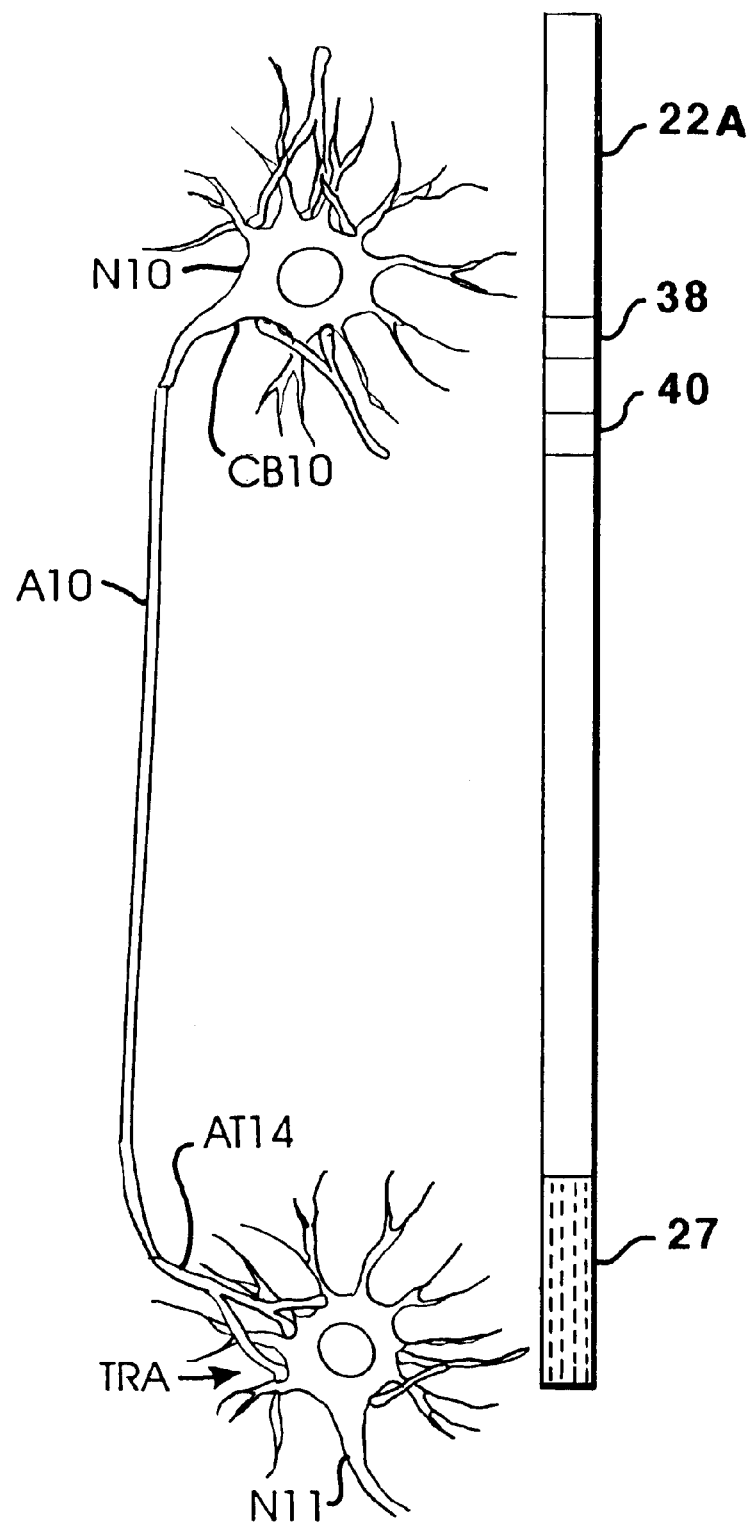

FIG. 21 illustrates a modified form of tube 22A in which infusion portion 27 is located more than 0.01 cm from electrodes 38 and 40 and infusion portions 28–29 have been removed. Neuron N10 has a cell body CB10 and an axon A10 that terminates in axon terminals AT14. A neuron N11 can be excited at axon terminals AT14 by an excitatory neurotransmitter TRA. Electrical stimulation of axon A10 causes the release of transmitter TRA at axon terminal AT14. Portion 27 is used to infuse an agent that blocks a degradative enzyme of transmitter TRA or an agent which blocks the reuptake of transmitter TRA. For each pulse administered by electrodes 38 and 40, the stimulation of neuron N11 is more potent. That is, more action potentials are generated in neuron N11.

Figure 16A:
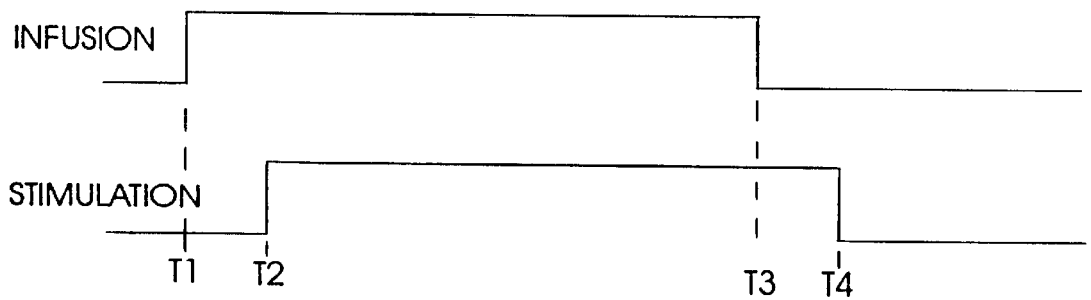
FIGS. 16A–16C are timing diagrams showing the relationship between the administration of drugs and electrical stimulation to nerve tissue.

FIG. 16A illustrates various times at which infusion and stimulation can be applied by tube 22A. For example, infusion alone can be applied from time T1 to T2, infusion and stimulation can be both be applied from time T2 to T3, and stimulation alone can be applied from time T3 to T4. This regimen might be used in the case when selective activation of one neuronal population is desired. By beginning the infusion before beginning stimulation during time T1 to T2, the threshold for electrical activation of one population of neurons can be lowered or raised as needed. Another example would be if a precursor molecule, such as L-dopa, is infused to guard against depletion of to the transmitter substance dopamine.

Figure 16B:
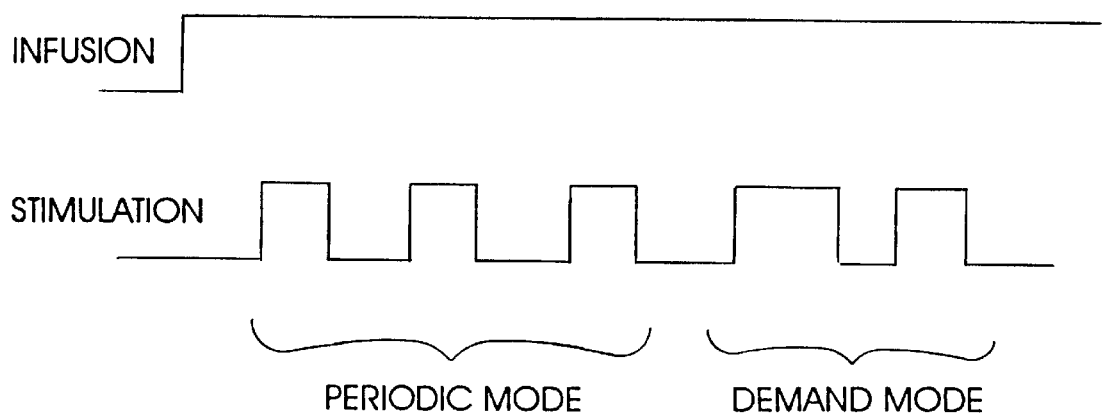

The stimulation might be applied periodically during the period of infusion either routinely or in response to sensor or patient generated demand as shown in FIG. 16B. Alternatively, stimulation could be applied continuously with infusion occurring periodically. Patient activation of either infusion or stimulation may occur as a result of an increase in symptoms being experienced by the patient.

Figure 16C:
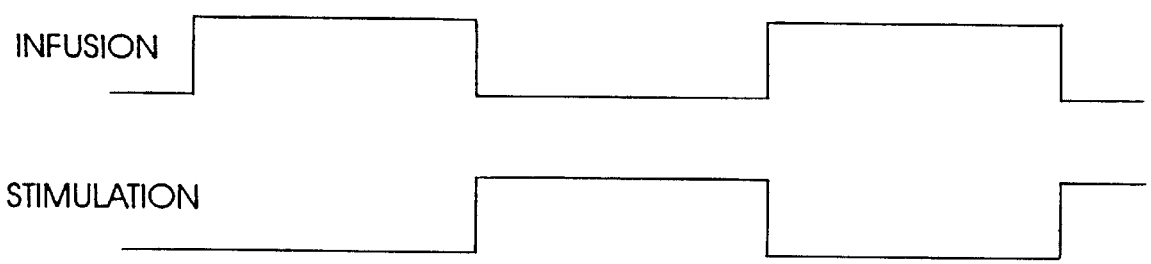

Alternatively, the infusion of an agent to activate a neuronal population might be alternated with application of electrical stimulation of that same population, as shown in FIG. 16C.

It also is possible to infuse an agent that has an affect upon the neuron population that is not strictly connected in time with the electrical depolarization of the neurons. In this case, the time of application of stimulation and infusion may be completely asynchronous. Or an agent could be infused that diffuses beyond the effects of the electrical stimulation but still has an advantageous effect on the brain independent of the stimulation effects.

In those instances where a continuous infusion of liquid agent is effective, the infusion device may be replaced with a static device such as is described in U.S. Pat. No. 4,892,538 which is incorporated by reference. An example of a static device is a device having a semipermeable wall enclosing encapsulated cells capable of secreting the appropriate agent. Alternatively, an implantable device could consist of a polymeric insert with the agent embedded within or on the surface of the polymer in such a way as to be slowly eluted from the polymer over time. Such a device is described in U.S. Pat. No. 4,346,709 "Drug Delivery Devices Comprising Errodable Polymer and Errosion Rate Modifier", Edward Schmitt Inventor, Issued Aug. 31, 1982, incorporated by reference and in U.S. Pat. No. 5,330,768 "Long-term Sustained Release Preparation." Yoshiya Yamahira et. al. Inventors, Issued Sep. 27, 1988. These alternative techniques could be employed with or without the simultaneous application of open-loop or closed-loop stimulation in the aforementioned manner.

By using the foregoing techniques for simultaneous drug infusion and electrical stimulation, anxiety disorders can be controlled with a degree of accuracy previously unattainable. Those skilled in that art will recognize that the preferred embodiments may be altered or amended without departing from the true spirit and scope of the invention, as defined in the accompanying claims.

I claim:

1. A method of using one or more drugs to therapeutically treat an anxiety disorder by means of an implantable pump and a catheter having a proximal end coupled to the pump and a discharge portion for infusing therapeutic dosages of the one or more drugs, the method comprising the steps of:
   surgically implanting the catheter so that the discharge portion lies in a brain parenchyma; and,
   operating the pump to discharge a predetermined dosage of the one or more drugs through the discharge portion of the catheter into the infusion site, whereby an anxiety disorder is treated.

2. The method of claim 1 wherein the step of surgically implanting comprises surgically implanting the catheter adjacent a predetermined infusion site in the brain tissue chosen to have anxiolytic properties.

3. The method of claim 2 wherein the step of surgically implanting the catheter adjacent a predetermined infusion site in the brain tissue chosen to have anxiolytic properties comprises the step of surgically implanting the catheter at the anterior limb of the internal capsule.

4. The method of claim 2 wherein the step of surgically implanting the catheter adjacent a predetermined infusion site in the brain tissue chosen to have anxiolytic properties comprises the step of surgically implanting the catheter at the head of the caudate nucleus.

5. The method of claim 2 wherein the step of surgically implanting the catheter adjacent a predetermined infusion site in the brain tissue chosen to have anxiolytic properties comprises the step of surgically implanting the catheter at the cingulum fibers.

6. The method of claim 2 wherein the step of surgically implanting the catheter adjacent a predetermined infusion site in the brain tissue chosen to have anxiolytic properties comprises the step of surgically implanting the catheter in the cingulate gyrus.

7. The method of claim 2 wherein the step of surgically implanting the catheter adjacent a predetermined infusion site in the brain tissue chosen to have anxiolytic properties comprises the step of surgically implanting the catheter at the dorsal medial nucleus of thalamus.

8. The method of claim 2 wherein the step of surgically implanting the catheter adjacent a predetermined infusion site in the brain tissue chosen to have anxiolytic properties comprises the step of surgically implanting the catheter at the locus ceruleus.

9. The method of claim 2 wherein the step of surgically implanting the catheter adjacent a predetermined infusion site in the brain tissue chosen to have anxiolytic properties comprises the step of surgically implanting the catheter at the amygdyla.

10. The method of claim 2 wherein the step of surgically implanting the catheter adjacent a predetermined infusion site in the brain tissue chosen to have anxiolytic properties comprises the step of surgically implanting the catheter at the dorsal raphe nucleus.

11. The method of claim 2 wherein the step of surgically implanting the catheter adjacent a predetermined infusion site in the brain tissue chosen to have anxiolytic properties comprises the step of surgically implanting the catheter at the septum.

12. The method of claim 2 wherein the step of surgically implanting the catheter adjacent a predetermined infusion site in the brain tissue chosen to have anxiolytic properties comprises the step of surgically implanting the catheter at the frontal cortex.

13. The method of claim 2 wherein the step of surgically implanting the catheter adjacent a predetermined infusion site in the brain tissue chosen to have anxiolytic properties comprises the step of surgically implanting the catheter at the anterior thalamus.

14. The method of claim 2 wherein the step of surgically implanting the catheter adjacent a predetermined infusion site in the brain tissue chosen to have anxiolytic properties comprises the step of surgically implanting the catheter at the mammillary body.

15. The method of claim 1 further comprising the step of sensing physiological parameters of a heightened state of anxiety.

16. The method of claim 15 wherein the step of operating the pump includes the step of controlling the operation of the pump, in response to the step of sensing physiological parameters, to discharge a predetermined dosage of the one or more drugs when a physiological parameter is detected.

17. A method of using one or more drugs to therapeutically treat an anxiety disorder by means of a static device capable of storing and releasing the one or more drugs when implanted in the central nervous system, the method comprising the steps of:
   surgically implanting the static device so that the one or more drugs may be released in the central nervous system;
   providing an electrical signal generator and an implantable electrode having a proximal end and a stimulation portion, the proximal end of the electrode coupled to the signal generator;
   surgically implanting the electrode so that the stimulation portion may stimulate a site in a central nervous system chosen to have anxiolytic properties;
   operating the signal generator to stimulate the chosen site in the central nervous system; and,
   treating an anxiety disorder with the drug that may be released into the central nervous system and stimulating the chosen site in the central nervous system.

18. The method of claim 17 further comprising the steps of:

sensing physiological parameters of a heightened state of anxiety; and wherein said step of operating the signal generator includes the step of operating the signal generator in response to the step of sensing physiological parameters, whereby the electrical signal produced by the signal generator is regulated in accordance with the physiological parameter detected.

19. The method of claim 18 wherein the step of sensing physiological parameters includes the step of implanting a sensor capable of sensing physiological parameters.

20. A method of using one or more drugs to therapeutically treat an anxiety disorder by means of an implantable pump and a catheter having a proximal end coupled to the pump and a discharge portion for infusing therapeutic dosages of the one or more drugs, the method comprising the steps of:

surgically implanting the catheter so that the discharge portion lies in an intrathecal space of a spinal cord; and, operating the pump to discharge a predetermined dosage of the one or more drugs through the discharge portion of the catheter into the infusion site, whereby an anxiety disorder is treated.

* * * * *